United States Patent [19]

Ford et al.

[11] Patent Number: 5,245,693
[45] Date of Patent: Sep. 14, 1993

[54] PARENTERAL FLUID WARMER APPARATUS AND DISPOSABLE CASSETTE UTILIZING THIN, FLEXIBLE HEAT-EXCHANGE MEMBRANE

[75] Inventors: Dixon Ford; Steven Ford, both of Farmington, Utah

[73] Assignee: In-Touch Products Co., Woods Cross, Utah

[21] Appl. No.: 669,825

[22] Filed: Mar. 15, 1991

[51] Int. Cl.⁵ .................. H05B 1/02; F24H 1/12; A61B 19/00
[52] U.S. Cl. .................. 392/470; 219/528; 165/170; 165/169; 165/46; 604/114
[58] Field of Search .................. 392/470, 485–489; 219/528; 165/170, 168–169, 46; 604/113–114; 137/341

[56] References Cited

U.S. PATENT DOCUMENTS

| | | | |
|---|---|---|---|
| 1,961,660 | 6/1934 | Fehrmann | 257/245 |
| 2,342,164 | 2/1944 | Pinkel | 257/245 |
| 2,424,792 | 7/1947 | Blum | 257/245 |
| 2,582,871 | 1/1952 | Kintner | 257/245 |
| 2,636,575 | 4/1953 | Watson | 183/114.2 |
| 2,690,653 | 10/1954 | Kleist | 165/170 |
| 2,766,514 | 10/1956 | Adams | 29/157.3 |
| 3,198,248 | 8/1965 | Stack | 165/166 |
| 3,293,868 | 2/1965 | Gonzalez | 62/3 |
| 3,327,776 | 6/1967 | Butt | 165/170 |
| 3,399,536 | 9/1968 | Walz | 392/470 |
| 3,443,060 | 5/1969 | Smith | 392/470 |
| 3,475,590 | 10/1969 | Pins | 392/470 |
| 3,485,245 | 12/1969 | Lahr | 128/272 |
| 3,590,215 | 6/1971 | Anderson | 392/470 |
| 3,590,917 | 11/1971 | Huber | 165/167 |
| 3,612,059 | 10/1971 | Ersek | 128/399 |
| 3,614,385 | 10/1971 | Horstmann | 392/470 |
| 3,640,283 | 2/1972 | Surindar | 128/399 |
| 3,718,182 | 2/1973 | Rosetti | 165/166 |
| 3,823,457 | 7/1974 | Staas | 29/157.3 D |
| 3,847,211 | 11/1974 | Fischel | 165/166 |
| 3,853,479 | 12/1974 | Talonn et al. | 165/46 |
| 4,038,519 | 7/1977 | Foucras | 392/470 |
| 4,108,146 | 8/1978 | Golden | 128/400 |
| 4,167,663 | 9/1979 | Granzow | 219/497 |
| 4,258,784 | 3/1981 | Perry | 165/166 |
| 4,287,883 | 9/1981 | Kyrias | 165/170 |
| 4,293,762 | 10/1981 | Ogawa | 392/470 |
| 4,309,592 | 1/1982 | Le Boeuf | 392/470 |
| 4,314,143 | 2/1982 | Bilstad | 219/497 |
| 4,356,383 | 10/1982 | Dahlberg et al. | 392/470 |
| 4,464,563 | 8/1984 | Jewett | 392/470 |
| 4,532,414 | 7/1985 | Shah | 392/470 |
| 4,540,412 | 9/1985 | Van Overloop | 604/291 |
| 4,574,876 | 3/1986 | Aid | 165/46 |
| 4,678,460 | 7/1987 | Rosner | 604/113 |

(List continued on next page.)

FOREIGN PATENT DOCUMENTS

| | | | |
|---|---|---|---|
| 2112006 | 6/1972 | France | 165/46 |
| 2403082 | 4/1979 | France | 392/470 |

Primary Examiner—Bruce A. Reynolds
Assistant Examiner—John A. Jeffery
Attorney, Agent, or Firm—Workman Nydegger Jensen

[57] ABSTRACT

An apparatus for heating parenteral fluids for intravenous delivery to a patient. The apparatus includes a disposable cassette which in one presently preferred embodiment is made up of a unitary member which is divided to form a serpentine flow path by a plurality of path separators. Thin, flexible metallic foil membranes are sealingly joined to the unitary member on the upper and bottom surfaces thereof to form an enclosed, fluid-tight serpentine flow path between the plurality of path separators. The entire periphery of the unitary member and the thin, flexible heat conductive foil membranes are sealingly held by a framework. The disposable cassette slides between first and second heating blocks which contact the thin, flexible heat conductive foil membranes so as to provide heat transfer to fluid flowing in the serpentine flow path. The heating blocks are designed to provide a gradation of heat energy such that more heat energy is available for transfer to the parenteral fluid at the inlet end of the serpentine flow path than is available for transfer to the parenteral fluid at the outlet end of the serpentine flow path.

40 Claims, 13 Drawing Sheets

U.S. PATENT DOCUMENTS

| | | | |
|---|---|---|---|
| 4,680,445 | 7/1987 | Ogawa | 392/470 |
| 4,707,587 | 11/1987 | Greenblatt | 392/470 |
| 4,731,072 | 3/1988 | Aid | 604/408 |
| 4,744,414 | 5/1988 | Schon | 165/167 |
| 4,759,749 | 7/1988 | Verkaart | 604/113 |
| 4,782,212 | 11/1988 | Bakke | 392/470 |
| 4,801,777 | 1/1989 | Auerbach | 219/10.55 |
| 4,844,074 | 7/1989 | Kureuz | 128/401 |
| 4,847,470 | 7/1989 | Bakke | 392/470 |
| 4,878,537 | 11/1989 | Verkaart | 165/156 |
| 4,906,816 | 3/1990 | van Leerdam | 392/470 |
| 4,908,014 | 3/1990 | Kroyer | 604/4 |
| 4,919,134 | 4/1990 | Streeter | 128/400 |
| 4,938,279 | 7/1990 | Betker | 165/46 |
| 4,962,761 | 10/1990 | Golden | 128/400 |
| 4,966,231 | 10/1990 | Belcher | 165/166 |
| 4,971,056 | 11/1990 | Seacord | 128/401 |
| 5,125,069 | 6/1992 | O'Boyle | 392/465 |

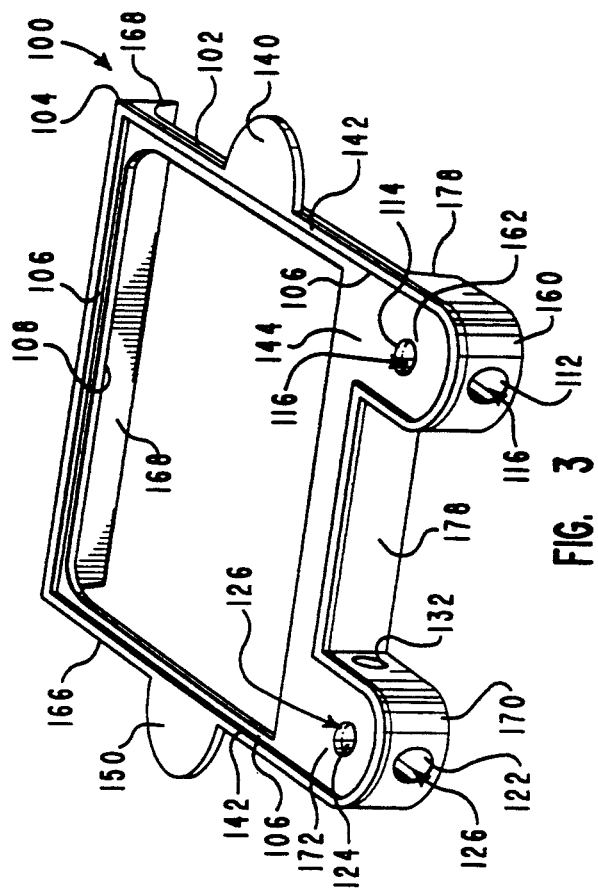
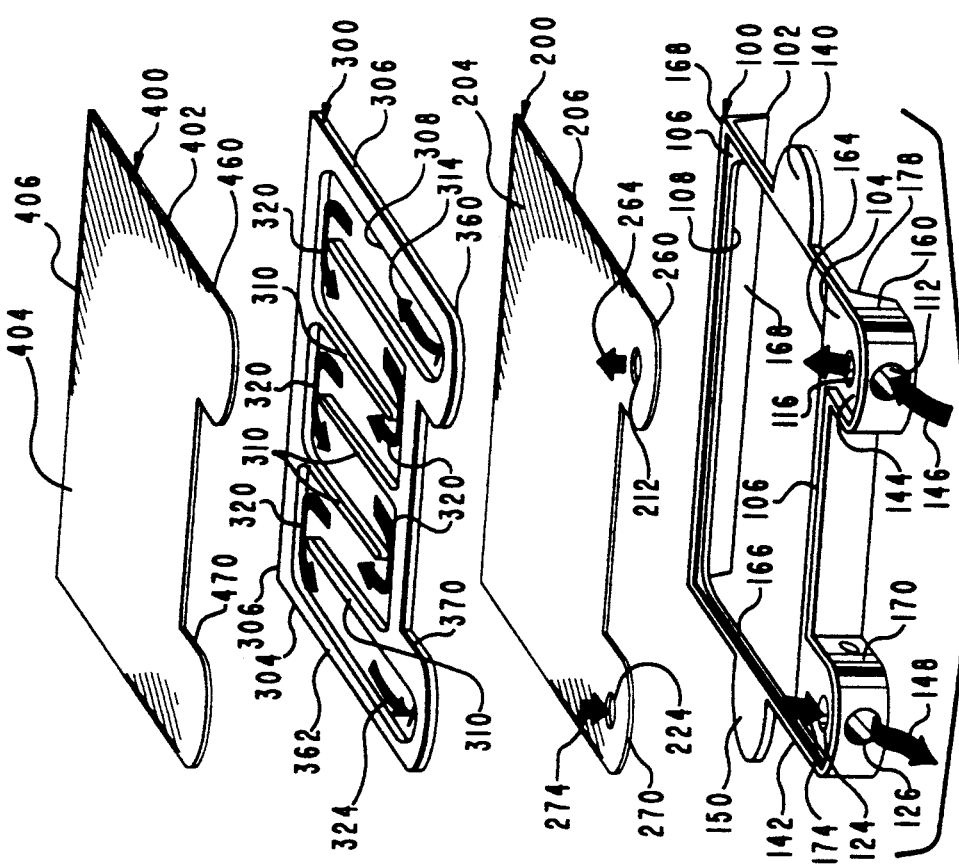

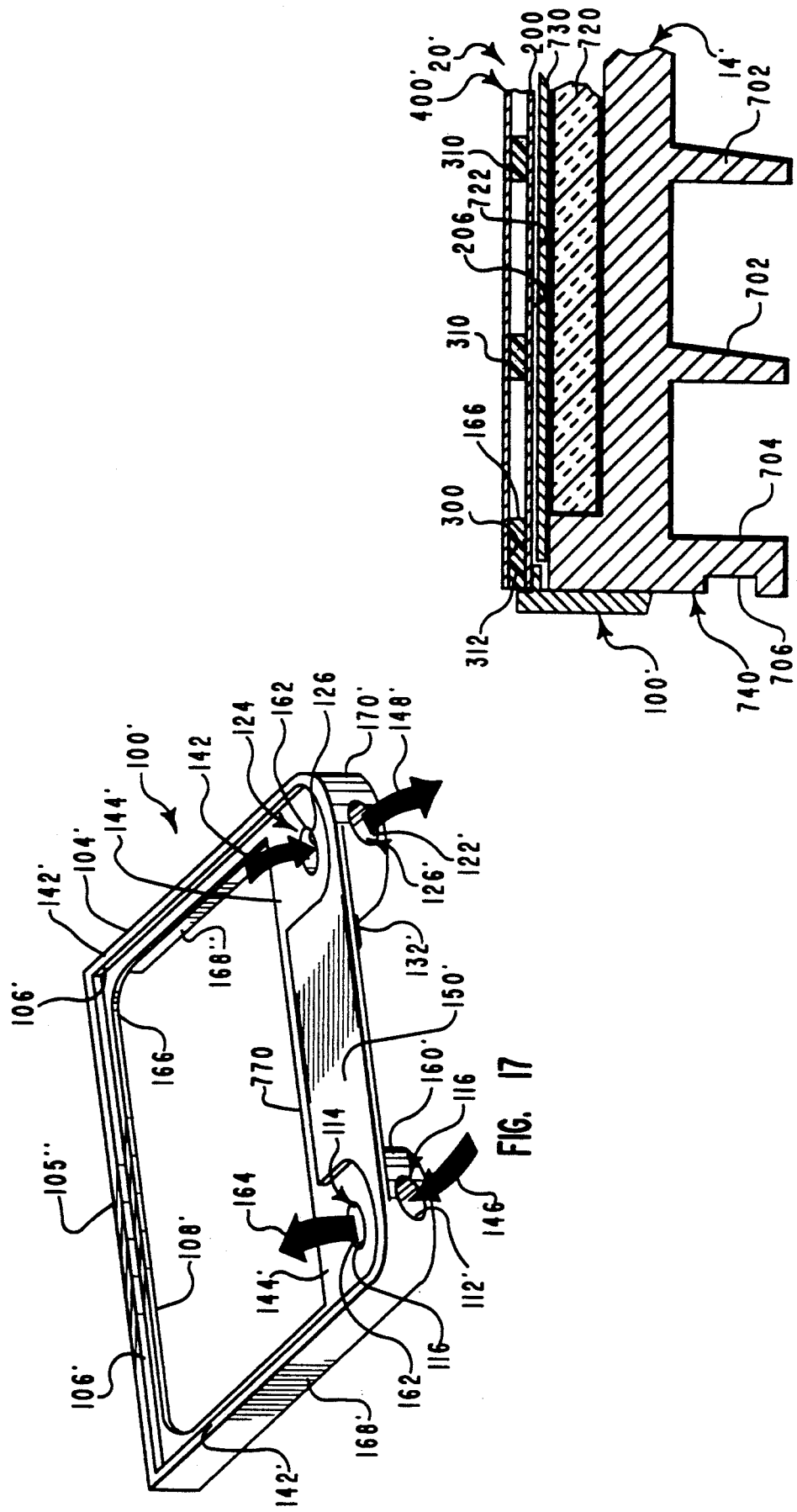

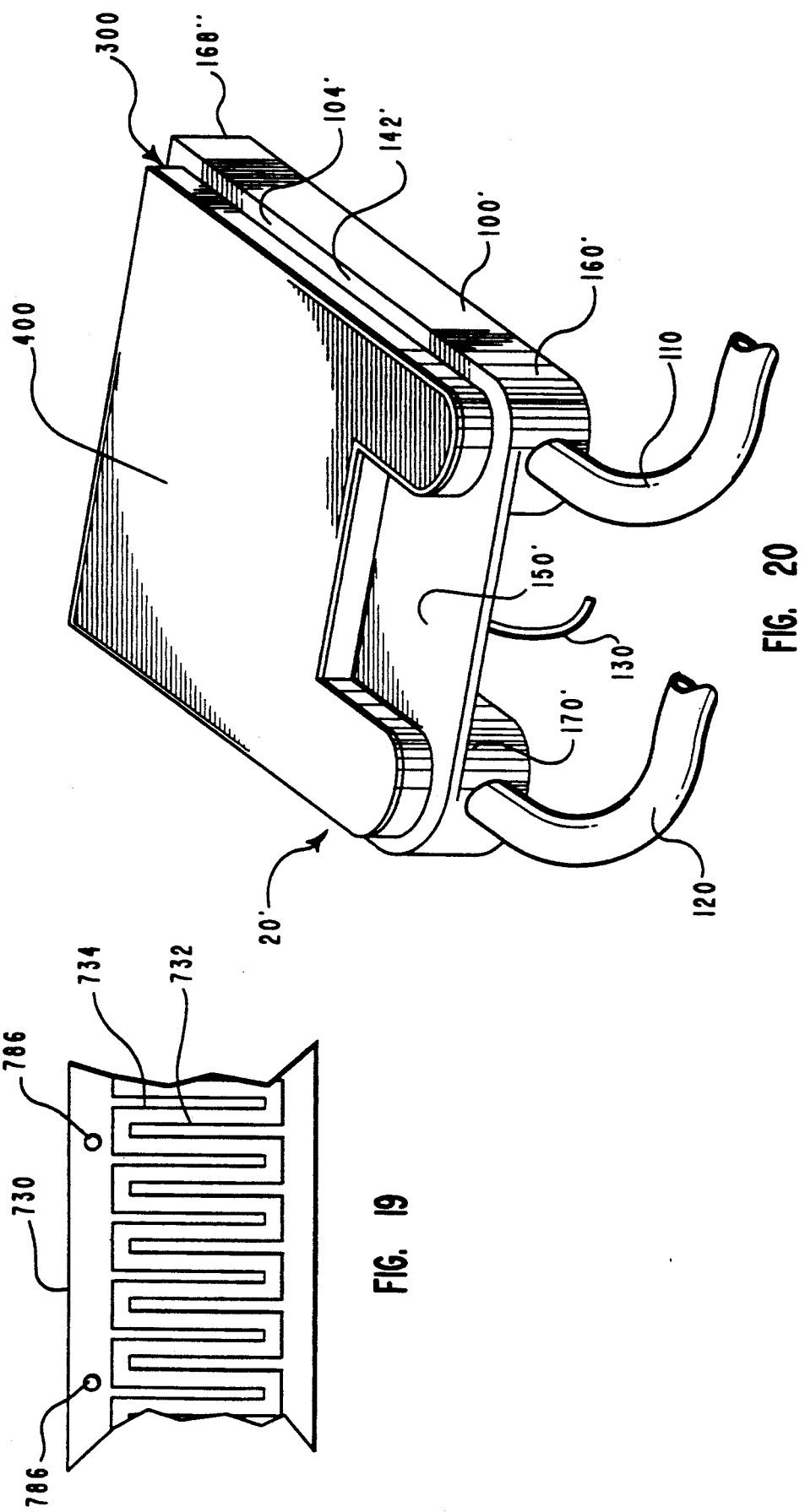

PARENTERAL FLUID WARMER APPARATUS AND DISPOSABLE CASSETTE UTILIZING THIN, FLEXIBLE HEAT-EXCHANGE MEMBRANE

FIELD OF INVENTION

This invention relates to parenteral fluid, especially blood, warming apparatus and more specifically to highly efficient heat transmitting disposable cassettes for use with heat providing and controlling apparatus and methods of manufacture and use of the disposable cassettes.

BACKGROUND AND DESCRIPTION OF RELATED ART

Blood and other parenteral fluids are commonly stored at hypothermic temperatures in the range of about 2°-10° Centigrade to maintain freshness and viability. Before such fluids are infused into a patient, it is common practice to raise the influent fluid temperature to nearly normal patient temperature levels of 36° to 38° Centigrade. In some cases, such as open heart surgery, it is desired to maintain the patient at hypothermic temperatures for a period of time and infuse blood at substantially the same hypothermic temperature. As such infusions varying rate and temperature, it is best to have in-line blood warming devices which warm the blood as delivery is made from a blood bag to the patient to conserve blood and reduce delays of off-line heating methods. A complication in the warming of viable physiologic fluids, such as blood, is a maximum safe temperature which may be used in the heating process. It is commonly known that the maximum safe temperature which may be used is in the range of 38° Centigrade. For these reasons, the safety and efficacy of imparting heat to blood and other parenteral fluids during infusion into a patient are critical parameters of an in-line heating device.

Generally, heat exchangers, not primarily meant for parenteral fluids heating, have comprised metallic or otherwise non-flexible, heat-exchanging plates, parts of which define circuitous passages for fluids in the heating pathways. U.S. Pat. Nos. 1,961,660, 2,424,792, 2,582,871, and 3,590,917 are examples of such heat exchangers. Devices which provide for heat exchange between fluids residing between juxtaposed parallel cavities are disclosed in U.S. Pat. Nos. 3,823,457, 4,258,784, and 4,744,414.

In some devices, it is important to avoid pressure buildup within a heating device, U.S. Pat. No. 3,718,182 teaches a heat exchange device wherein outlet pipes are made of a larger diametral size than the inlet pipe to reduce internal pressure buildup. Internal pressure has been used to fashion hollow metal articles using high input pressure in the forming process as disclosed in U.S. Pat. No. 2,766,514.

A plurality of physiologic fluid heaters are known in the art. Devices for heating parenteral fluids, especially blood, comprise water, air, and electrical plate modalities. As an example, U.S. Pat. No. 4,678,460 teaches a heater for parenteral fluids which comprises a water warmer and a bubble rap for eliminating air from the parenteral fluid. Another water heater which heats blood flowing through a coiled tube is taught in U.S. Pat. No. 3,614,385. U.S. Pat. No. 4,707,587 describes an air circulating heater which measures the incoming and outgoing temperatures of both blood and the heat transporting air. U.S. Pat. No. 4,759,749 discloses a sterilizable metal heat exchanger for physiological fluids.

Much of the known related art teaches heating parenteral fluids or blood in disposable devices employing tubes or bags.

As an example of a tube employing device, U.S. Pat. No. 4,532,414 discloses an in-line fluid warmer for parenteral fluids. The fluid warmer includes a box-like enclosure containing a heated plate having a sinuously-shaped groove to accept and hold a length of conduit in heat exchanging relationship. U.S. Pat. No. 4,293,762 discloses another heater comprising a serpentine pattern wherein a tube through which fluid to be heated flows.

While it is common to use a heater bag which comprises a labyrinth on serpentine path wherein the fluid is heated as it courses a relatively long pathway across heating elements. U.S. Pat. No. 4,309,592 discloses a bag and device mostly open to upwardly directed fluid flow. A restrictor is employed between an inlet pipe and main portion of the fluid path of the bag to restrict travel of the fluid introduced by the inlet pipe to maintain substantially homogeneous flow throughout the main portion of the fluid path, thereby providing more even heating of fluid within the bag. U.S. Pat. No. 4,464,563 teaches a hollow cylindrical polystyrene or polycarbonate cassette heated by two heating elements, one heating element disposed in the inner core of the cassette is heated to a higher temperature while the other heating element disposed around the outer surface of the cylinder is heated to a lower temperature.

U.S. Pat. No. 4,844,074 teaches a two stage heater for physiological fluids wherein fluid is pumped through a regulated heater into a gravity-feed container, then led by gravity flow out of the gravity-feed container through the same heater to the organism being infused. The heater comprises a bag, having a serpentine fluid path, which is disposed between heating and sensing plates.

U.S. Pat. No. 3,485,245 discloses a heater comprising two plates, each of which comprises a serpentine passageway wherein a disposable bag comprising a similar serpentine blood path is placed. U.S. Pat. No. 3,590,215 also teaches a bag or sac which comprises a serpentine pathway wherein blood is heated as it flows therethrough, but heat is supplied by pivotally mounted, thermally conductive flat plates which are in heat conductive relation with the sac. Each heating element is tapered form the inlet end to the outlet end so that the heat output diminishes in proportion to the diminishing rate of heat absorption of fluid moving from the sac inlet to the sac outlet. The shape of the heating elements are calculated to be direct functions of thermal conductivity of the sac, an important parameter due to relatively high thermal insulating qualities of plastics.

Another blood warming apparatus comprising a bag with a serpentine path is disclosed in U.S. Pat. No. 4,167,663. An apparatus is disclosed therein which comprises a control circuit responsive to the input and output temperature of the fluid being heated and heating elements which respond to signals from the control circuit. U.S. Pat. No. 4,314,143 discloses an apparatus for warming blood and other parenteral fluids through a disposable fluid system comprising a warming bag and primarily disposed to solving problems related to electrical controls and monitoring of the heated fluids.

U.S. Pat. No. 3,640,283 discloses an attachment to a plastic envelope heat sealed to form a tortuous fluid flow conduit therein. The attachment provides a drip chamber whereby air is removed as the blood flows from an outlet of the envelope.

U.S. Pat. No. 4,906,816 discloses a blood heating apparatus, comprising a box provided with a hinged door. Blood flows through a plastic pouch having a labyrinth-shaped pathway. The doors are provided with temperature controlled electrical heating assemblies which contact both sides of the pouch when the hinged door is closed, suspension pins assure position of the pouch relative to the box and door.

U.S. Pat. No. 4,680,445 discloses a heating bag disposed between modified heating plates having ridges which contour the bag thereby reducing outgassing in The bag. The bubbles which result from outgassing insulate the blood and make heating less efficient. Such outgassing is caused by the mass of the blood weighing against the bottom of each segment of the bag thereby deforming the bag and creating a negative pressure at the top of each segment of the bag where the outgassing occurs. The ridges comprise a form which reduces deformities of the bag thereby reducing the insulating bubbles.

BRIEF SUMMARY AND OBJECTS OF THE INVENTION

In brief summary, this novel invention provides a surprisingly effective parenteral fluid and blood warming apparatus. The invention comprises a disposable cassette and related methods of manufacture and use whereby fluid is efficiently warmed by a single pass through the disposable cassette. Further, the invention comprises an apparatus whereby an additional element of safety is maintained by monitoring and comparing the temperature indicating signals from a plurality of sensors imbedded in heating plates as the heating plates are activated to warm fluid flowing in the interposed disposable cassette. In addition, a further safety measure comprises monitoring the conductivity of the heating elements within each heating plate.

The cassette comprises a frame which connects to inlet and outlet tubes and provides fluid pathways to and from the tubes to the fluid heating parts of the cassette its supports. Juxtaposed and adhesively affixed on the top of the frame is a first foil layer. A layer comprising a spacer is juxtaposed and affixed on top of the first foil layer. Finally a second foil layer is juxtaposed and affixed on top of the spacer to complete assembly of the cassette. Each foil layer is selectively treated to be physiologically inert relative to parenteral fluid or blood, thereby providing a heating plate to foil to fluid thermal pathway for more efficient heating with less hat transfer lag than experienced with parenteral fluid heaters which comprise a plastic membrane disposed between the heating plate and the fluid.

The first foil layer comprises a first hole wherethrough fluid received in the inlet tube flows from the frame into a serpentine path defined by the spacer layer. The first and second foil layers are sealed to the spacer to maintain fluid flow within the serpentine path. The first foil also comprises a second hole at the outlet end of the serpentine path wherethrough fluid flows into the outlet port of the frame.

The frame comprises an opening which exposes substantially the entire heating surface of the first foil. Heating is accomplished by placing the foils in relatively high pressure contact with the heating plates which are heated to a temperature required to warm fluid to a preset set point. Full contact between each foil and heating plate is assured by placing a fluid resistance in the outlet of the frame and providing an upstream pressure on the fluid at the inlet such that each foil is forced outward above the serpentine path against each heating plate, thereby enhancing the contact area between the foil and each heated plate. Each set point temperature to which fluid is heated is user variable and is set in a range from hypothermic temperatures for hypothermically maintained patients in nearer normal physiological temperatures in the range of 37° Centigrade. In no case can a set point be entered which exceeds a predetermined maximum temperature in the range of 38° Centigrade.

Higher than ambient internal pressure in the cassette not only assures a full and pressured contact against each heating plate, but also ensures against the generation of outgassing bubbles which may otherwise occur due to negative pressures resulting from gravity caused deformations in flexible parts. The elimination of potential outgassing allows the cassette to be oriented for use in any plate. Use of fluid contacting, heat conducting foils in direct pressure contact with the heating plates provides a fluid warmer of surprising efficiency.

Cassette manufacture is at least partially automated.

The heating plates comprise increased thermal mass in cross section and heating elements which comprise greater heat output capacity in areas where heat transfer is the greatest. In addition, the heating plates comprise electrical connections and side rails providing insertion guides whereby each plate is releasibly inserted into the instrument housing and thereby electrically connected as a modularly replaceable part.

The instrument provides housing and control for the cassette and heating plates. The instrument also comprises temperature and status displays and switches on a control panel user interface. A frame comprising the top rail guide is reciprocally operated to release and apply pressure between the heating plates wherein the cassette is inserted. Thereby, a cassette is facilely inserted and firmly held in position while parenteral fluid is passed therethrough and safely and efficiently heated.

Accordingly, it is a primary object to provide a cassette for a parenteral fluid or blood heater which safely and efficaciously heats the parenteral fluid or blood.

It is another primary object to provide a cassette for a parenteral fluid or blood heater which is disposable.

It is another primary object to provide an apparatus which releasibly houses the disposable cassette.

It is another primary object to provide at least one frame within the housing which releasibly accommodates at least two heating plates.

It is another primary object to provide the at least two heating plates disposed within the frame to juxtapose an interposed cassette placed therebetween.

It is another primary object that a portion of the at least one frame be reciprocally adjustable whereby the cassette is placed under pressure between the heating plates while fluids are being warmed and released from such pressured containment or removal and replacement.

It is a dominant object to provide the disposable cassette with foil membranes attached to and separated by a spacer comprising a serpentine path wherethrough fluid flows while warming.

It is a further dominant object to provide the cassette with foil members which are flexible.

It is another dominant object to provide a restrictor in the effluent path of the cassette whereby fluid flowing under pressure into the cassette creates a greater than ambient static pressure inside the cassette.

It is another dominant object to provide pressurized contact between the heater plates and sandwich comprising the foils and the spacer which exceeds and the static pressure inside the cassette.

It is an object to provide expansion of the foils to make firm contact over substantially the entire heating surface of the cassette with each heating late when fluid flows through the cassette.

It is another dominant object to provide a foil which is physiologically inert to blood and other parenteral fluids thereby providing a heating plate to foil to fluid path for efficient thermal conduction.

It is another object to provide a raised surface on one of the heating plates which matches a surface accessing opening of the cassette thereby providing direct contact between the heating plate and foil interface while providing accurate, facile positioning of the cassette within the apparatus during replacement.

It is a key object to provide a sensor in the effluent path of the cassette for a safety check and feedback for a temperature display and alert.

It is another key object to provide a plurality of heating elements in each heating plate for redundancy and distribution of the sources of heat.

It is another key object to provide heating elements and heating plates comprising power and mass distribution, respectively, which is substantially proportional to the rate of heat absorption of the fluid being heated as it flows through the cassette.

It is another key object to test current flow through the heating elements and provide an alert, indicating failure of a heating element, if the current flow is not within predetermined tolerance limits.

It is another key object to measure the temperature of each thermally separate section and provide an alert if measured temperatures do not agree within predetermined limits.

It is a chief object to provide a controller comprising a micro-processor, memory, and an analog to digital converter.

It is another chief object to provide a controller which comprises temperature measurement, memory for storing the measurements, and programming to compare and display measurements.

It is another chief object to provide a controller providing control of the heating elements.

It is another chief object to provide an operator control panel comprising displays of set point temperature, effluent heated fluid temperature, and heating plate temperatures and controls for adjusting the set point, for releasing compressive pressure on the cassette for removal and replacement, and for controlling audio ALARM ON/OFF.

It is a further chief object to provide ALARM, ALERT and ready indicators on the operator control panel.

It is a still further chief object to provide an alpha-numeric display whereby causes of alarms and alerts are displayed.

It is another chief object to provide a time-sharing of the alpha-numeric display comprising presentation of heating plate temperatures during periods of normal operation when alerts and alarms are not on.

It is another chief object to provide an instrument ready indication on the alpha-numeric displays.

These and other objects and features of the present invention will be apparent from the detailed description taken with reference to accompanying drawings.

BRIEF DESCRIPTION OF THE DRAWINGS

FIG. 2 is an exploded perspective of the cassette wherein four layered parts are seen.

FIG. 3 is a perspective of a frame for the cassette which is the first on lower layer in the cassette.

FIG. 17 is a perspective of another embodiment of a blood warming frame for a cassette.

FIG. 18 is a segmental portion of a cross section of a lower or bottom low inertial mass heater and of a blood warming cassette placed thereupon.

FIG. 19 is a section of a heating element for the low initial mass heater seen in part in FIG. 18.

FIG. 20 is a perspective of the blood warming cassette which employs the frame of FIG. 17.

DETAILED DESCRIPTION OF THE ILLUSTRATED EMBODIMENTS

Figure 1:
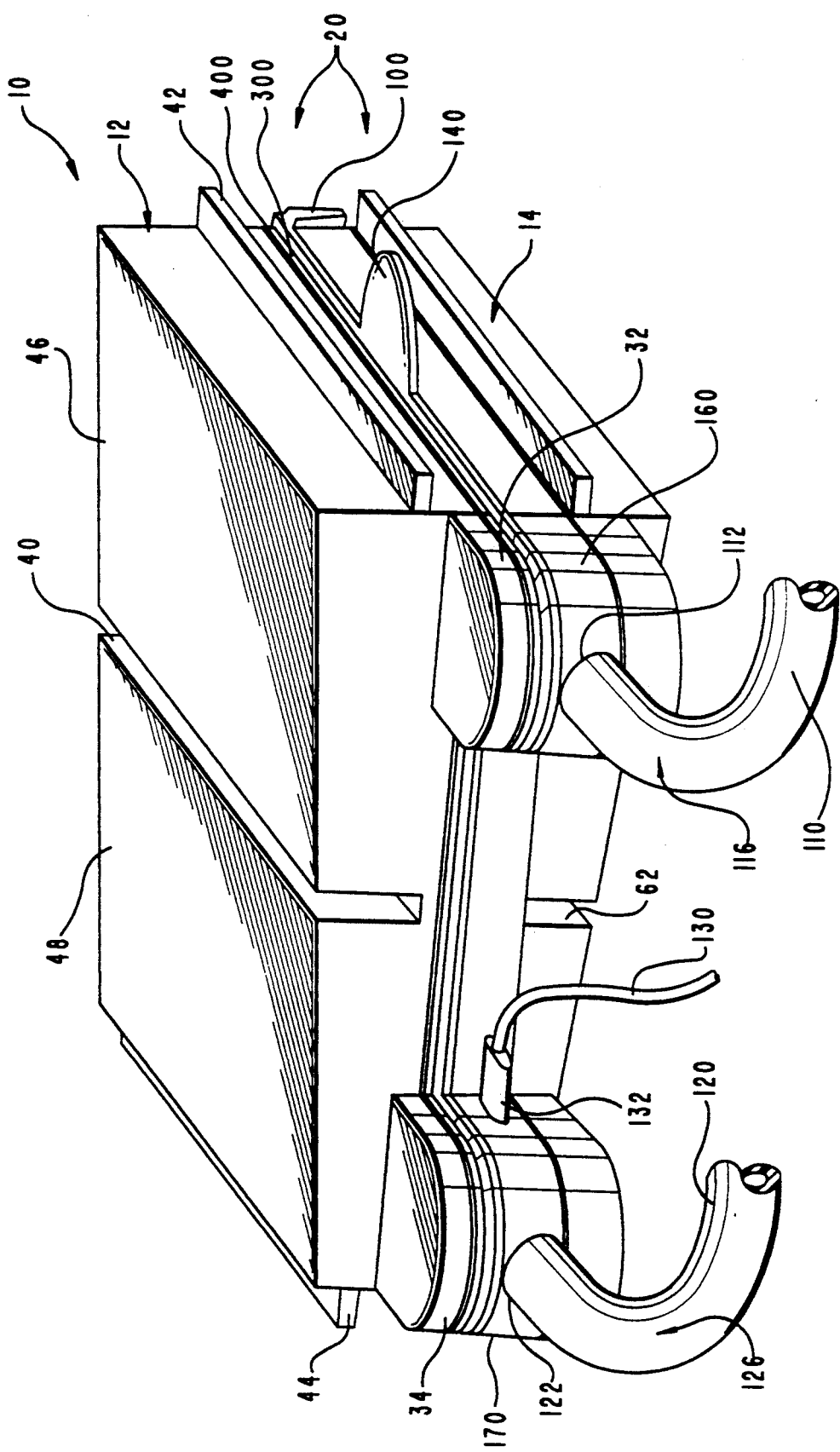
FIG. 1 is a perspective of a parenteral fluid heating assembly comprising a blood warming cassette, wherethrough, parenteral fluid flows, disposed between two trapezoidal heating plates.

In this description, the term proximal is used to indicate the segment of the device normally closest to the operator when it is seen or being used. The term distal refers to the other end. Reference is now made to the embodiments illustrated in FIGS. 1-20 wherein like numerals are used to designate like parts throughout. A currently preferred embodiment of a parenteral fluid heating assembly 10 is seen in FIG. 1. Parenteral fluid heating assembly 10 comprises a fluid heating cassette 20 disposed between an upper heating plate 12 and a lower heating plate 14.

Cassette 20 comprises efficient thermal communication with heating plates 12 and 14 through direct contact between the heating plates 12 and 14 and foils which are also in direct contact with fluid flowing through cassette 20 as is described in detail hereafter. Fluids enter into cassette 20 through inlet tube 110 and exit toward an infusion site through outlet tube 120. Inlet tube 110 and outlet tube 120 are firmly sealed to cassette 20 by adhesives or other bonding agents. Tubes 110 and 120 may be vinyl tubes commonly used in medical IV applications. Adhesives and other bonding agents for affixing vinyl tubes to other synthetic resinous materials are well known and available in the art. As is common practice when infusing intravenous fluids, a bubble trap (not shown) is disposed between a patient and the cassette when in normal use. A fluid temperature sensor 130 is disposed in the outlet blood path which provides a signal which is sampled and converted to a digital number for blood temperature display and for computer based automatic checking and generation of an alert in the event outlet blood is outside preset limits.

Cassette 20 is comprised of four parts, a frame 100, a lower heat transmitting layer 200, a spacer 300, and an upper heat transmitting layer 400, as seen in FIG. 2. Frame 100 provides structural support for the other parts of cassette 20. As is better seen in FIG. 3, frame 100 comprises a distal support 168, a proximal side member 102, a distal side member 166, and a proximal support 178. Disposed proximally from proximal support 178 is a right pedestal 160 and a left pedestal 170 each of which is connected to proximal support 178 by a top support plate 104 in the plane of side members 102 and 166. Frame 100 is fabricated by molding or machining from rigid, synthetic resinous material which is essentially inert to parenteral fluids. A material such as cyrolyte may be used for frame 100.

Distal support 168 comprises a vertically oriented planar strip substantially disposed across the width of cassette 20. Proximal support 178 also comprises a vertically oriented planar strip substantially disposed across the width of cassette 20. The two supports 168 and 178, in combination, provide a stand for frame 100 and also provide guide members for inserting cassette 20 into a position of use as is described in detail later.

Frame 100 comprises an attachment port 112 for inlet tube 110 in pedestal 160. Attachment port 112 is sized and shaped to accept plastic inlet tube 110, as seen in FIG. 1. Plastic inlet tube 110 is selected from materials generally used for parenteral fluid transport in medical practice. Similarly, pedestal 170 comprises an attachment port 122 for outlet tube 120. Tube 120 is essentially the same tubing material as inlet tube 110. Pedestal 170 comprises another port 132 wherethrough a temperature sensor 130 is inserted and firmly affixed with an leak-proof seal.

Pedestal 160 comprises a right angle flow path 116 as signified by arrows 146 and 164 in FIG. 2. Pedestal 160 comprises an orifice 114 through top support plate 104 where inlet flow enters cassette 20. Frame 100 comprises a thin ridge 142 which is disposed on top support plate 104 around the perimeter of the top of frame 100. Disposed medially from ridge 142 in top support plate 104 is a lower surface 144, separated from ridge 142 by a rim 106, best seen in FIG. 3. Lower surface 144 comprises a medial access 108 wherethrough an opening is provided in top plate 104. The use and function of opening 108 is described in detail hereafter.

Figure 9:
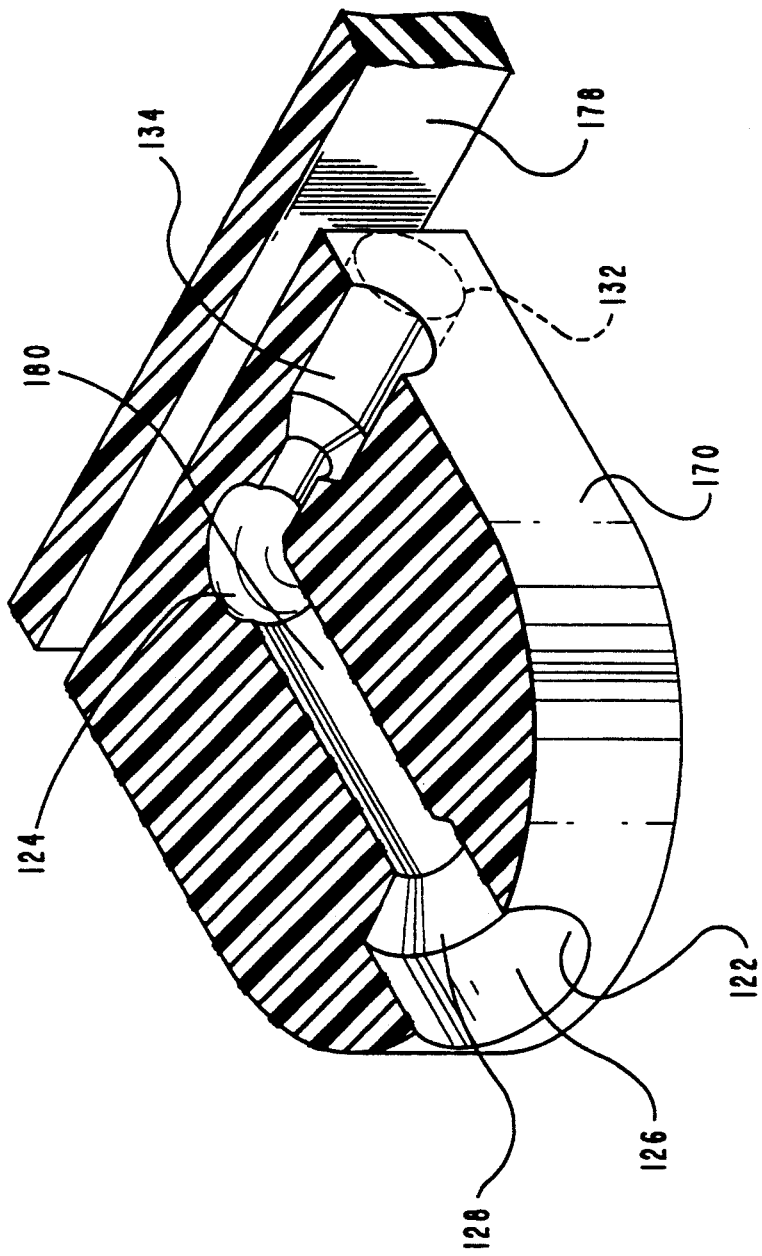
FIG. 9 is a sectional slice along 9—9 of FIG. 3.

Pedestal 170 comprises an outlet orifice 124 and right angle flow path 126. However, as seen in FIG. 9, flow path 126 is partially interrupted by a flow restrictor 180 thereby providing a flow path of reduced diameter relative to the diametral size of outlet orifice 124 and inlet orifice 114. Restrictor 180 produces a measurable pressure drop across flow path 126 thereby providing a greater than ambient pressure in cassette 20 when pressurized fluid is flowing therethrough.

Pedestal 170 also comprises a temperature sensor port 132 wherein sensor 130, seen in phantom lines in FIG. 9, is inserted to measure fluid flow temperature in outlet path 126. Fluid contacting parts of sensor 130 are sterilizable and covered by a material which is essentially physiologically inert. Such sensors are known and available in the art.

Referring again to FIG. 3, a depression is formed around the edges of orifice 114 in top surface 144 of top plate 104 of such a thickness that an adhesive 162 placed therein fills the depression without rising substantially above surface 144. A similar depression wherein adhesive 162 is disposed is formed about orifice 124. Adhesive 162 is also disposed on top surface 144 along medial access opening 108. Adhesive 162 may be a thermal or other adhesive selected from adhesives which are known and available in the art.

Figure 4:
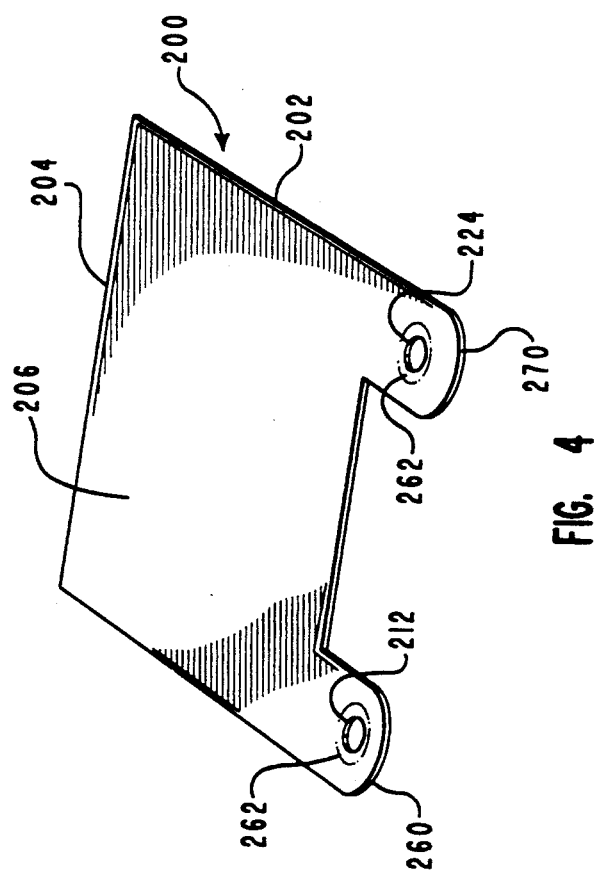
FIG. 4 is a perspective of a thin metallic foil which is disposed in direct contact with the frame to make a second layer.

As seen in FIGS. 2 and 4, a thin foil, which may be metallic or other material which is highly thermally conductive and essentially inert to physiological fluids provides a first heat conductive layer 200. Such a layer 200 may be silver plated copper. Such a silver plated copper foil may be in the range of 0.0005 to 0.005 inches thick. The silver plating may be on the order of 0.00005 inches thick. Layer 200 comprises a rectangular shape having a top surface 204, a bottom surface 206 attached to a proximally extending right ear 260 and a proximally extending left ear 270. Layer 200 is seen bottom-side-up in FIG. 4. Ear 270 comprises an orifice 224 which is surrounded by a ring of adhesive 262 on bottom surface 206. Similarly, ear 260 comprises an orifice 212 which is surrounded by a similar ring of adhesive 262. Adhesive 262 may be as adhesive 162.

The perimeter 202 of layer 200 comprises a shape which nests within rim 106 when layer 200 is juxtaposed against frame 100. The height of rim 106 is greater than the thickness of layer 200. Layer 200 may be in the range of 0.002 to 0.005 inches in thickness, while the depth of rim 106 may be in the range of 0.035 inches. To attach layer 200 to frame 100, layer 200 is nested on surface 144 within the perimeter of rim 106. When disposed thereat and firmly attached thereto, orifice 224 is juxtaposed and aligned with orifice 124 and orifice 212 is juxtaposed and aligned with orifice 116, thus providing continuous fluid pathways, as indicated in FIG. 2 by arrows 274 and 264, respectively.

Figure 5:
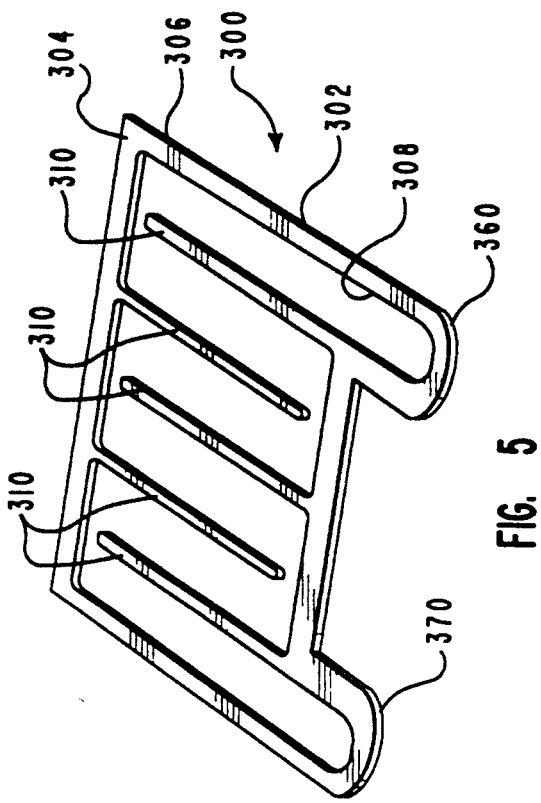
FIG. 5 is a perspective of a spacer which is disposed on top of the second layer and defines a path for parenteral fluids.

A flowpath determining spacer 300 is seen in FIGS. 2 and 5. As seen in FIG. 5, spacer 300 is a planar part of homogenous thickness which defines a serpentine path 308 comprising a length which is long relative to a width which is wide compared to a depth which is essentially the thickness of an edge 302. The thickness of edge 302 is in the range of 0.040 inches. The pat is formed by stamping or machining and deburred to eliminate any rough edges whereat blood or other active fluids may accumulate and react. Spacer 300 is made from physiologically inert materials which adhesively attach to layer 200 and layer 400. Such materials are known and available in the art. Spacer 300 comprises an outer perimeter 312 of essentially the same shape and size as that of layer 200 such that spacer 300 also nests within rim 106 when spacer 300 is juxtaposed and aligned with layer 200 such that extending ears 360 and 370 are juxtaposed with ears 260 and 270, respectively.

Figure 6:
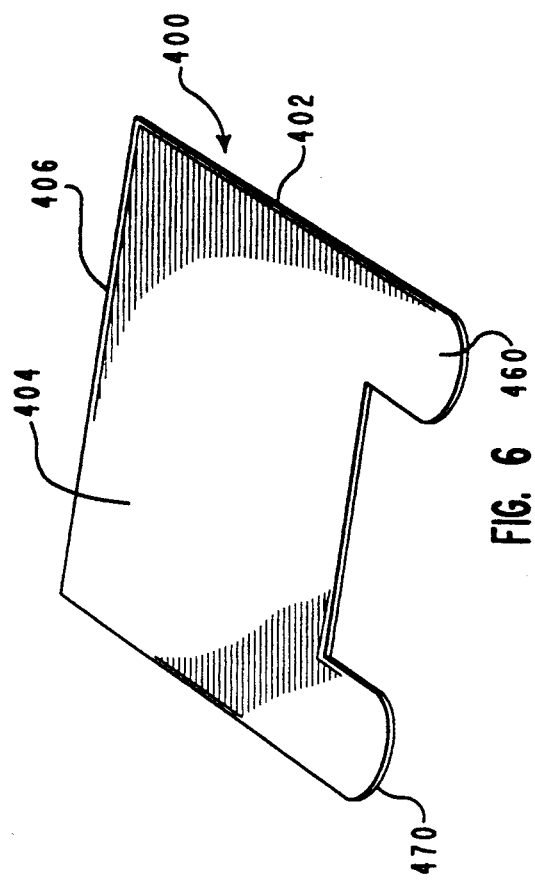
FIG. 6 is a perspective of a thin metallic foil which is disposed on top of the spacer to provide uppermost containment of the parenteral fluid.

As seen in FIG. 5, spacer 300 comprises a mostly open medial section providing the serpentine path defined by medial edge 308. A series of path separators 310 extend proximally and distally to separate and effectively lengthen the fluid flow path. In cross section, path separators may be in the range of three-sixteenths of an inch wide and 0.040 inches wide. Separator 310 dispostion within spacer 300 provides a pathway in the range of five-eighths of an inch wide and 0.040 inches high. As seen n FIG. 2, the fluid follows a path defined by an inlet defining arrow 314, a plurality of arrows 320 in seriatim, and an outlet defining arrow 324. When spacer 300 is placed on layer 200 and disposed within rim 106 a free path comprising the flow path defined by arrows 146, 164, 264, 314, 320, 324, 274, 174, and 148 trace input to output flow. A top layer 400, seen in FIGS. 2 and 6, is placed and affixed by adhesive 362 to spacer 300 to provide a topmost containment.

Spacer 300 comprises a homogeneous layer of adhesive 362 on top surface 304 and bottom surface 306. By such, each layer 200 and layer 400 is adhesively attached to spacer 300 thereby forming the contained serpentine path wherein the fluid is heated. As seen in FIG. 6, top layer 400 comprises essentially the same shape, including two ears 460 and 470, as spacer 300 and layer 200. However, the only shaping requirement for layer 400 is for the serpentine path to be completely covered and the peripheral edge 402 of layer 400 be reasonably free of edges which provide opportunity for catching and tearing. The combined thickness of layer 200, spacer 300, and layer 400 is greater than the thickness of rim 106 such that when frame 100, layer 200, spacer 300 and layer 400 are assembled to form cassette 20, the top side 404 of layer 400 is accessible by the bottom 22 of an associated planar top heating plate 12.

Figure 7:
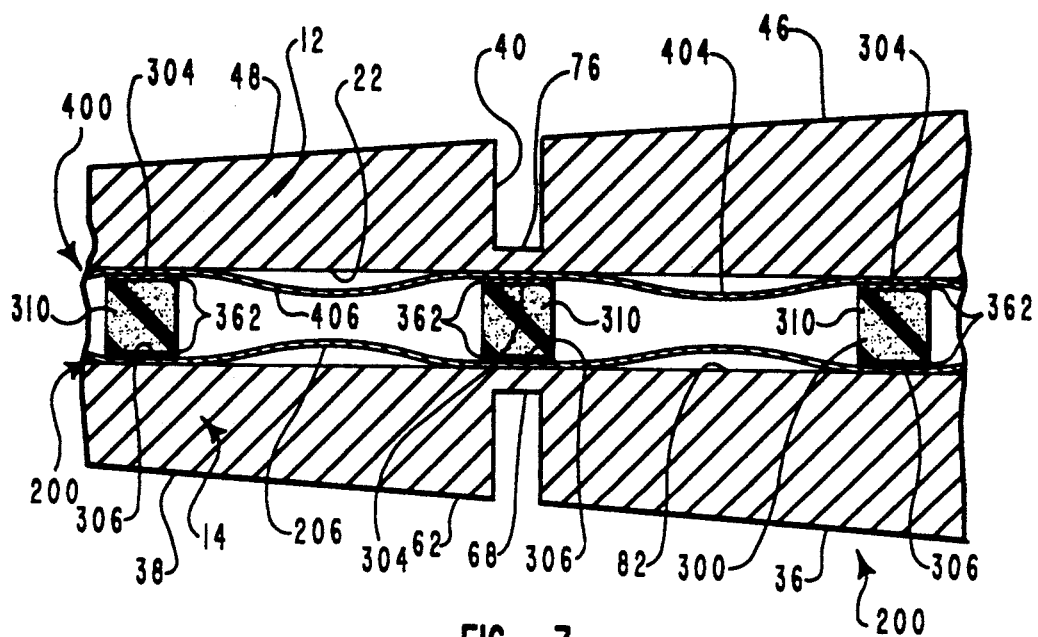
FIG. 7 is a section along lines 7,8—7,8 of FIG. 1.

As mentioned earlier, when a pressurized fluid flows through cassette 20, restrictor 180 causes an above ambient backpressure in cassette 20. Referring to FIG. 7, a cross section of a portion of heating assembly 10 is seen wherein the heating plates 12 and 14 are tightly clamped upon cassette 20, making firm contact above and below supports provided by spacer 300 parts. As shown in FIG. 7, the supporting parts comprise path separators 310. In the vicinity of each separator 310, close contact is maintained between the upper surface 404 of layer 400 and the bottom surface 22 of heating plate 12 and the lower surface 206 of layer 200 and the top surface 82 of bottom heating plate 14. However, in between the supporting parts, inherent flexibility and lack of other support allows each foil layer 200 and 400 to separate from direct contact with heating plates 12 and 14. The separation between the foil layers 200 and 400 and associated heating plate surfaces 82 and 22, is magnified in FIG. 7 for clarity of presentation; however, poor thermal conductivity of an air space resulting from any separation causes a marked degradation in he efficiency of a heater.

Figure 8:
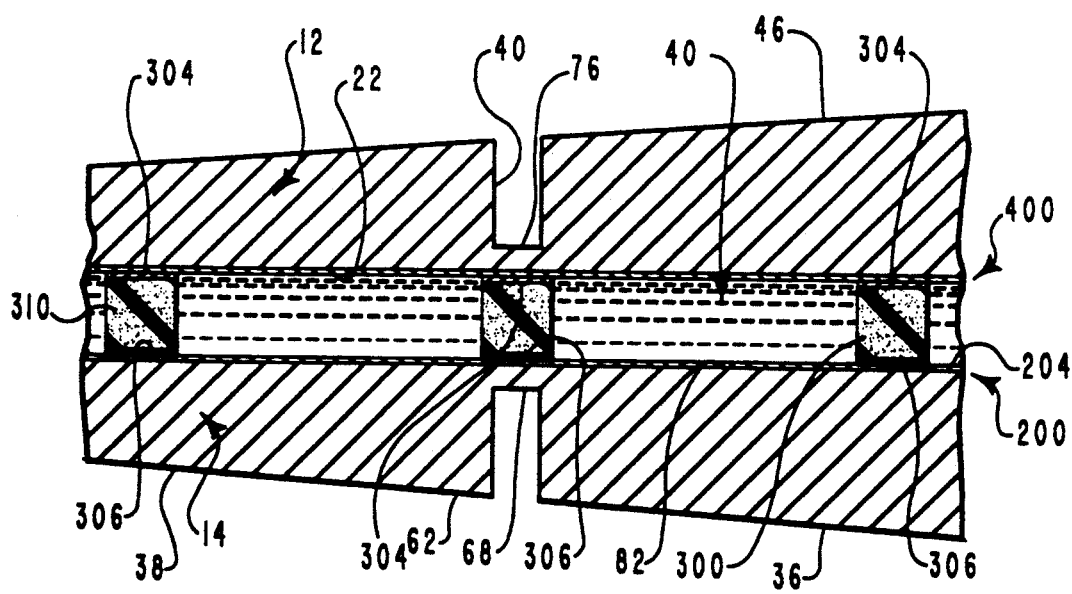
FIG. 8 is a section along lines 7,8—7,8 of FIG. 1.

As seen in FIG. 8, when cassette 20 is filled with pressurized fluid 444, greater than ambient static pressure on inner surfaces 406 and 204 forces layer 400 and 200, respectively, outward. As a result outer surfaces 206 and 404 are forced to be flush against surfaces 82 and 22, respectively. This close forcing contact between layers 200 and 400 and surfaces 22 and 82 provides a contact of very low thermal resistance. The high conductivity of the foils of layers 200 and 400 further increase the efficiency of thermal conductance.

It is well known int eh art that lower than ambient pressures result in outgassing from parenteral fluids which provokes the formation of bubbles along a flow path. In some cases, distortion of plastic bags and other flexible containers in some heaters create such negative pressures with resulting bubble formation. Bubbles disposed across an otherwise useful thermal conductive path significantly reduce heater efficiency. The higher than ambient static pressure within cassette 20 essentially eliminates outgassing and formation of bubbles within the flow path.

Figure 12:
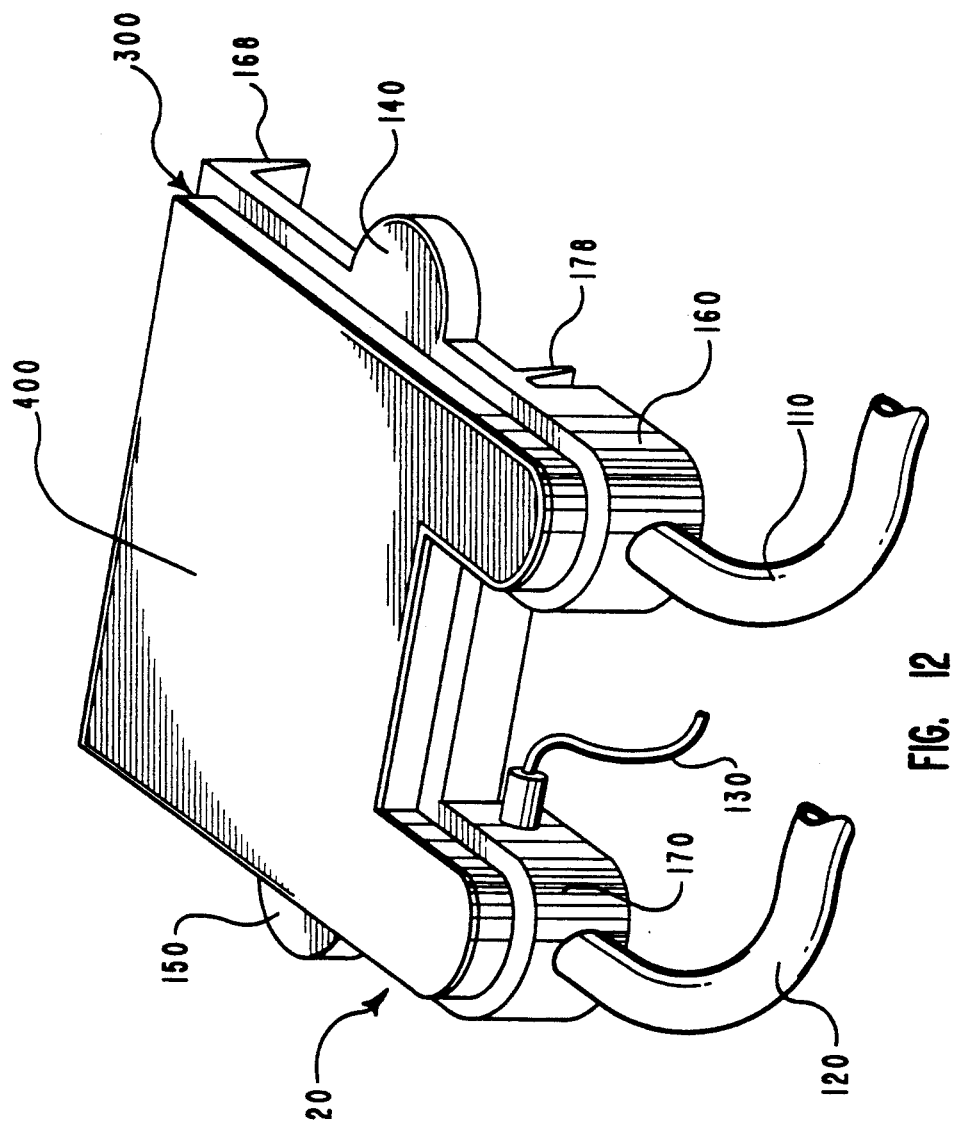
FIG. 12 is a perspective of the blood warming cassette.

As seen in FIG. 2, frame 100 also comprises a tab 140 on which is a semicircular extension of top plate 104 about the mid-point of side 102. Another tab 150 is similarly shaped and disposed as an extension of top plate 104 about the mid-point of side 166. Tabs 140 and 150 provide handles for use in handling cassette 20 and for use in inserting cassette 20 between heating plates 12 and 14. A fully assembled cassette 20 is seen in FIG. 12.

Referring again to FIG. 1, cassette 20 is disposed between top heating plate 12 and bottom heating plate 14 which, in combination with cassette 20, comprise the three components of heating assembly 10. Top heating plate 12 is reciprocally moved up and down as shown by arrow 464 to release and make pressurized contact with cassette 20. Bottom heating plate 14 provides a static mounting surface for cassette 20.

Figure 13:
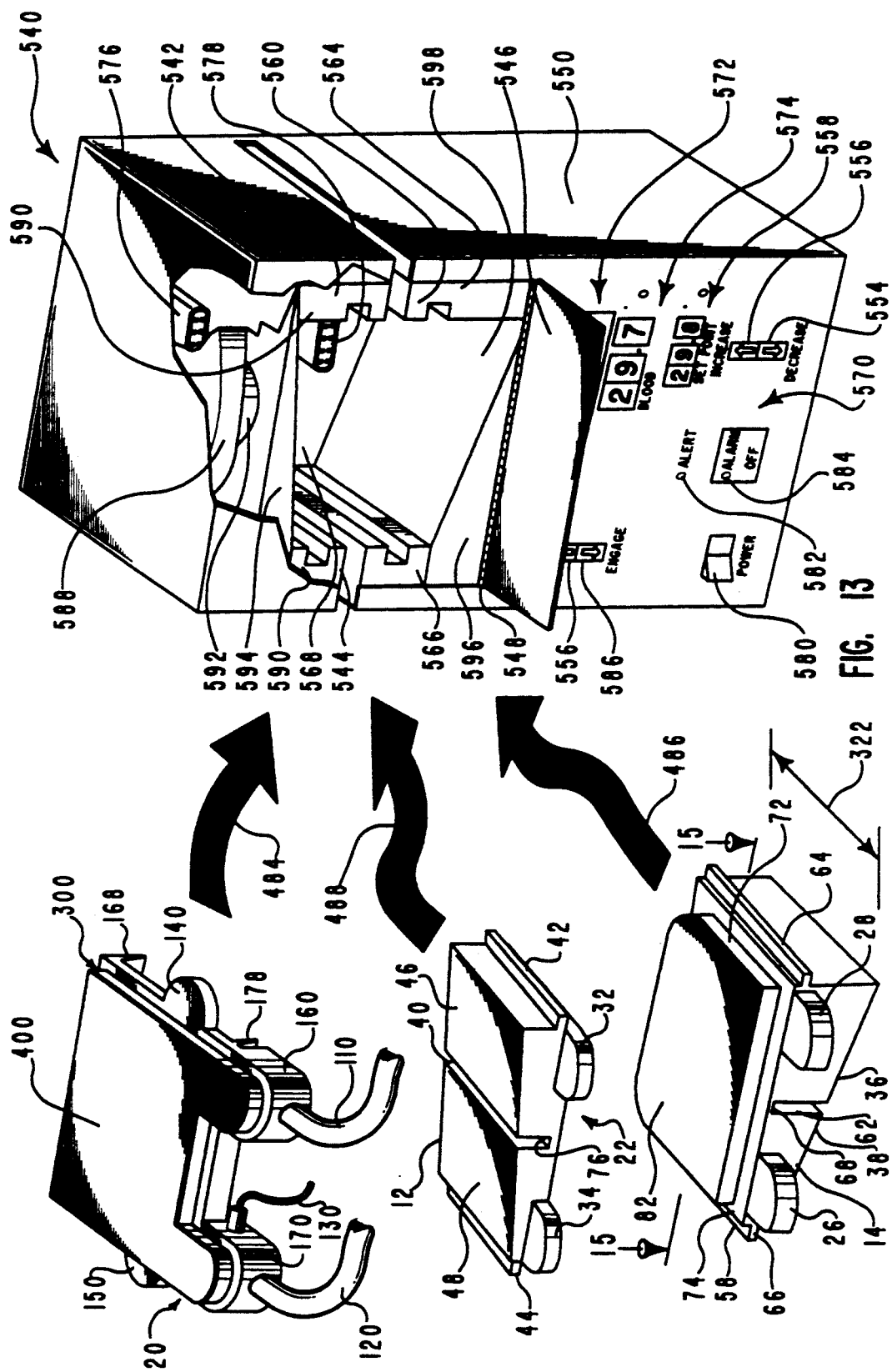
FIG. 13 is an exploded perspective of a fluid heating assembly and associated housing and control apparatus.

The three components of heating assembly 10 are better seen in FIG. 13. In this currently preferred embodiment, bottom heating plate 14 is rectangularly trapezoidal. The height of side 30, which is disposed on the inlet side of cassette 20 is greater than the height of outlet side 58 thereby providing greater mass of heating plate 14 where fluid heat absorption is the greatest.

Bottom plate 14 comprises a planar top surface 82. Planar top surface 82 comprises a shape which conforms to the size and shape of medial access 108 of frame 100 as seen in FIG. 3 such that when cassette 20 is set upon bottom plate 14 surface 82 nests within medial access 108 and directly contacts surface 206 of layer 200. A peripheral rim 72 around surface 82 is therefore thicker than rim 108. Further the width dimension of bottom plate 14, seen as dimension line 322 is shorter than the normal distance between proximal support 178 and distal support 168. Thereby, cassette 20 straddles bottom heating plate 14 when mounted thereon.

Bottom heating plate 14 comprises a pair of guide rails 64 and 66 disposed equidistant from surface 74 on opposite sides 30 and 58, respectively, and provides guide rails for facile insertion of bottom heating plate 14 into a heating instrument 540, also seen in FIG. 13. Heating instrument 540 comprises a pair of rail guides 564 and 56 for accepting insertion of bottom heating plate 14. Prior to use, bottom heating late 14 is inserted with rails 64 and 66 dovetailing with rail guides 564 and 566 and fully inserted until an electrical male connector (not shown) on the distal side of bottom heating element 14 engages with a female connector 542 distally disposed in instrument 540, thereby providing power and control connections. Male/female connectors for such slide in connections are known and available in the art.

Figure 15:
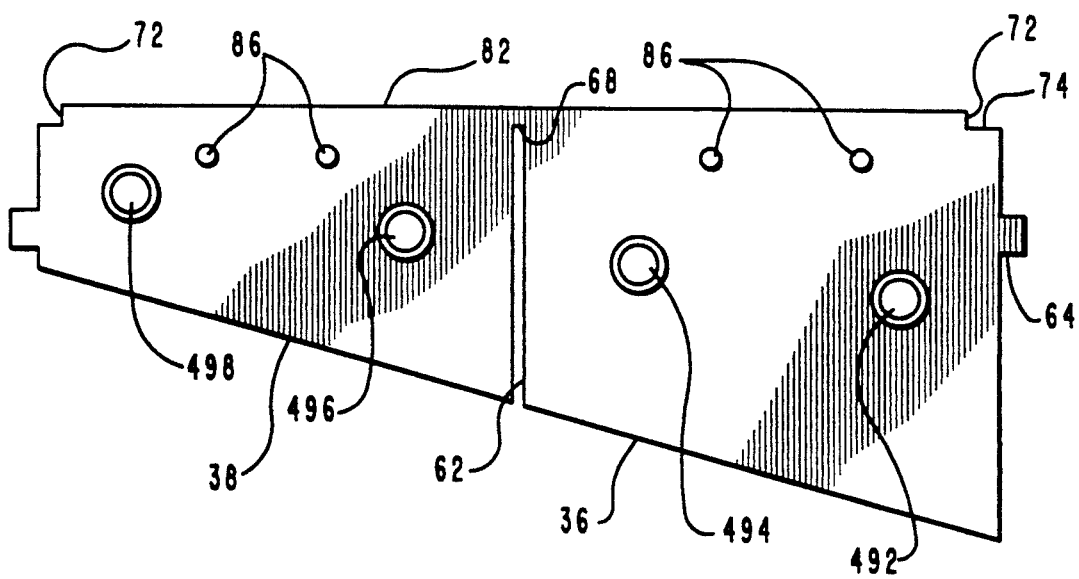
FIG. 15 is a cross section along lines 15—15 of FIG. 13.

Heating of bottom heating plate 14 comprises a combined function of a plurality of heating elements, which are better seen in FIG. 15. In the currently preferred embodiment, for heating elements 492, 494, 496, and 498 comprise a gradation of power output. Heating element 492, disposed in the thicker portion of bottom heating block 14, comprises the highest wattage in the range of 400 watts, while heating element 498 is the lowest wattage in the range of 150 watts. Heating element 494 is in the range of 300 watts, and heating element 496 is in the range of 200 watts. Of course, use of heating elements comprising different numbers of elements and power ratings is within the scope the invention. Such heating elements are known and available in the art.

Bottom heating plate 14 is substantially divided into two thermally separated sections 36 and 38 by a channel 62. Channel 62 provides an upward cut to a base 68 leaving adequate material for physical strength, but significant thermal isolation between the sections 36 and 38. As seen in FIG. 15, two temperature sensors 86 are disposed in each section 36 and 38 for reasons which are described in detail later.

Referring again to FIG. 13, a pedestal support 28 is disposed on the right proximal side of section 346 at a level which provides support, protection and thermal contribution, for cassette 20 pedestal 160 when cassette 20 is disposed on bottom heating plate 14. A second pedestal support 26 is disposed on the left proximal side of section 38 for similar protection and support of pedestal 170.

As seen in FIG. 13, rectangular trapezoidal top heating late 12 is similar, but disposed as a mirror image, to bottom heating plate 14. Bottom surface 22 is flat to compressively and fully contact the top surface 404 of layer 400. The trapezoidal structure of heating plate 12 comprises the greatest mass near the connection of inlet tube 110 when heating plate 12 is juxtaposed with cassette 20.

Top heating plate 12 also comprises guide rails, one guide rail 42 being disposed on the inlet port 112 side and another guide rail 44 being disposed on the outlet port 122 side. Heating instrument 540 comprises a pair of rail guides 542 and 544 for accepting insertion of guide rails 42 and 44, respectively. Thereby, heating plate 12 is releasibly inserted into hating instrument 540 and electrically connected, in similar fashion to bottom heating plate 14, to a female connector 576 seen through a cut-away of parts of instrument 540 in FIG. 13. Top heating plate 12 comprises four heating elements 492, 494, 496, and 498 having similar power ratings and positions relative to those previously described for bottom heating plate 14.

A further similarity to bottom heating plate 14 is the division of top heating plate 12 into two thermally separated sections 46 and 48 by a channel 40 which provides a downward cut to a base 76 which provides thermal separation while affording adequate material strength to compress against cassette 20 without substantial geometric distortion of bottom plate 22.

Top heating plate 12 comprises four temperature sensors 86 in similar relative disposition to the temperature sensors 86 in bottom heating plate 14. Top heating plate 12 comprises a pedestal shield disposed to provide protection and thermal contribution above each of the pedestals of cassette 20. When cassette 20 is disposed below top heating plate 12, pedestal shield 32 is juxtaposed above pedestal 160 and pedestal shield 34 is juxtaposed above pedestal 170, thereby providing a protection against inadvertent upward movement of the cassette 20 pedestals.

To complete the assembly of instrument 540, top plate 14 is slidably inserted into rail guides 542 and 544 in a direction indicated by arrow 488 until connector 576 connects with the male connected on the distal side of top plate 14 and bottom plate 12 is likewise inserted into rail guides 564 and 566 in a direction indicated by arrow 486. Rail guides 542 and 544 are part of a vertically reciprocable frame 590. Frame 590 comprises a top guide plate 594, which substantially comprises the same slant along a bottom surface 568 as that of sections 46 and 48 of top heating plate 1, and connection to an air cylinder 588 through a biaxial articulating joint 592 disposed therebetween. Articulating joint 592 allows the plane of surface 22 of top heating plate 12 to conform to the plane of each cassette 20 disposed thereunder when frame 590 is lowered to compressively sandwich cassette 20 between heating plate 12 and 14.

A frame 560 comprises rail guides 564 and 566 and a cavity, bounded on the bottom by slanted surface 598 of lower mounting plate 596, which is sized and shaped to releasibly accept insertion of bottom heating plate 14. Frame 560 provides static support first for bottom heating plate 14 and therefore for cassette 20 when residing thereupon and for top heating plate 12 when compressively lowered to rest upon cassette 20.

Figure 14:
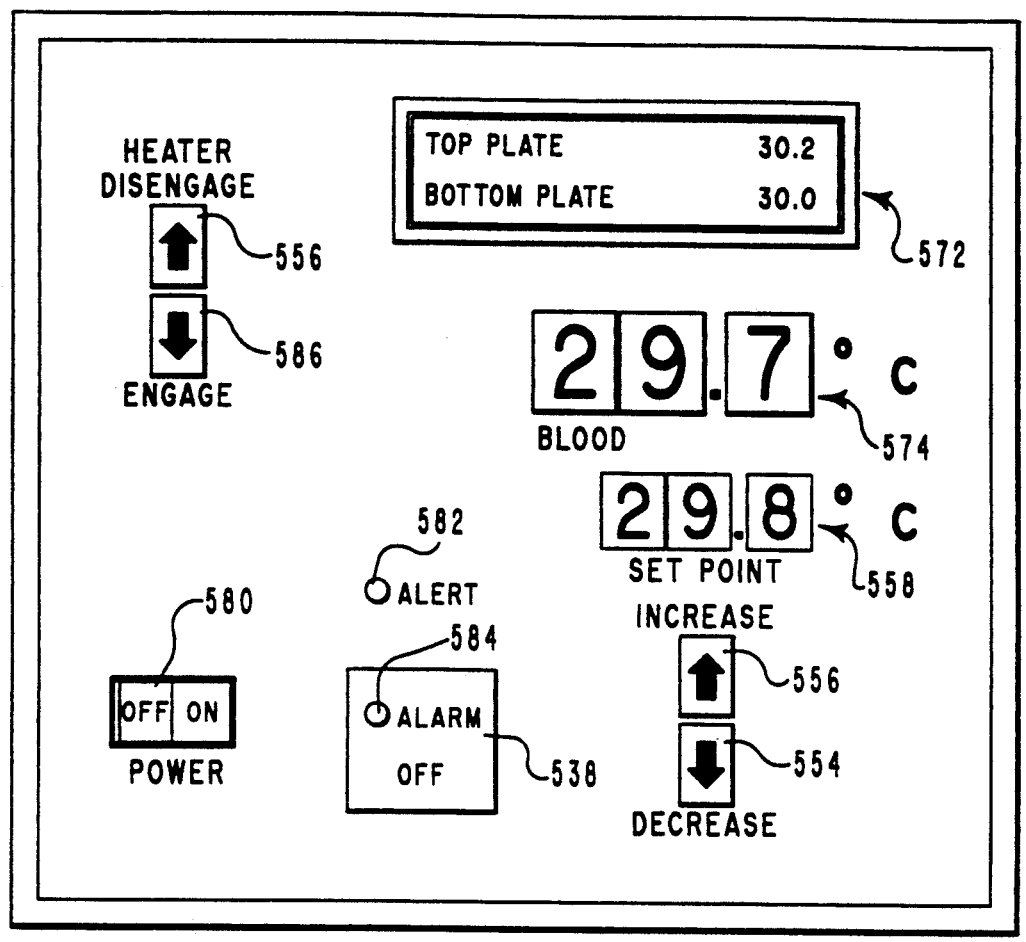
FIG. 14 is a layout of a control panel of the heating and control system.

Instrument 540 comprises a control panel 570 whereby a user controls insertion and extraction of cassette 20 and ascertains the status of instrument 540 operation. As seen in FIG. 14, control panel 570 comprises an alpha-numeric display 572, a blood, or other parenteral fluid temperature display 574, a set point temperature display 558, an ALERT indicator 582, a video ALARM indicator 584, an audio ALARM toggle switch 538, a frame 590 DISENGAGE control switch 556, a frame 590 ENGAGE control switch 586, a set point temperature INCREASE switch 556, a set point temperature DECREASE switch 554 and a power ON/OFF switch 580.

Figure 16:
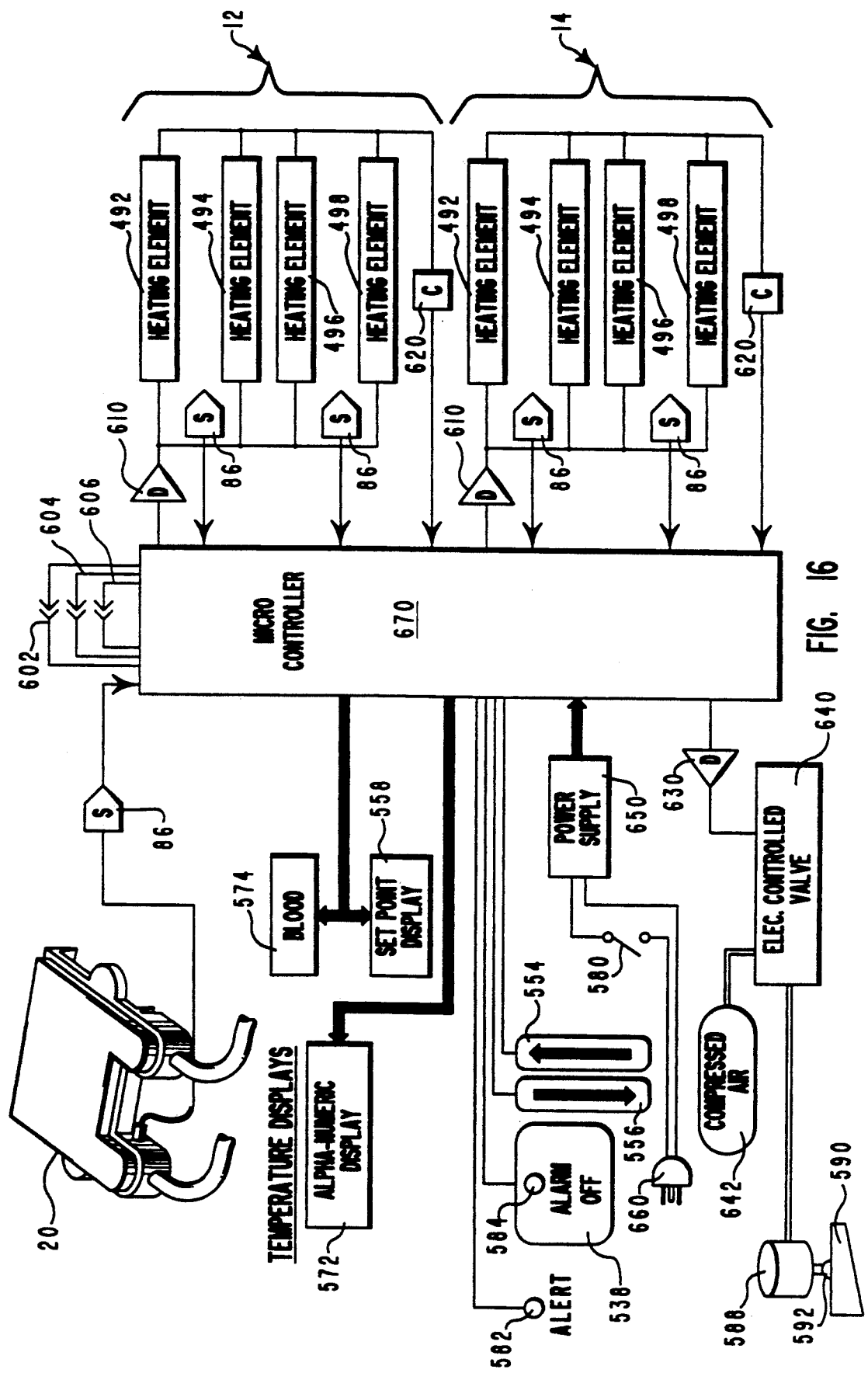
FIG. 16 is a block diagram of a heating and control system of the fluid heating system.

Control panel 570 comprises the user interface for an electrical control system 680 seen schematically in FIG. 16. All of the components of electrical control system are commercially available and are used in a manner well known in the art. Electrical control system comprises a micro-controller 670, heating element drivers 610, conductance sensing circuits 620, a power supply 650 and power cord and connector 660, an electrical driver 630 for an electrically controlled pneumatic valve 640, and interconnections to control panel 570 components and other electrical components such as connectors 576 and 542 seen in FIG. 13. In the currently preferred embodiment, alpha-numeric display 572 in a two-line by twenty-four character liquid crystal display although other displays and display sizes are within the scope of the invention. Displays 574 and 558 are three digit numerical displays. Video indicators 584 and 582 are light emitting diodes, although other displays and indicators may be used within the scope of the invention.

Micro-controller 670 comprises memory, an A/D converter, and a micro-processor by which electrical control system 680 is programmably controlled. Identical thermal control interfacing circuits are provided for top heating plate 12 and bottom heating plate 14. For this reason, only the thermal control for bottom heating plate 14 is described.

Conduction in heating elements 492, 494, 496, and 498 is controlled as sensors 86 provide measurements of temperature which are below and above preset limits for a previously selected set point temperature. As seen in FIG. 14, depression of switch 556 raises the value of a micro-controller 670 stored set point temperature which is displayed on set point temperature display 558.

Depression of switch 554 reduces the stored and displayed set point temperature.

As earlier related, heating plate 14 comprises four temperature sensors 86, two in each thermally separated section 36 and 38. In addition, a temperature sensor 86 is disposed in cassette 20 for measuring fluid temperature at outlet port 122. The temperature of each sensor of each pair of temperature sensors in each thermally separated section 36 and 38 in heating plate 14 is sensed and compared with the other sensor of the pair. If agreement, within tolerable limits, is found between each pair of heating plate 14 sensors 86, the mean value of the four measured temperatures is calculated and displayed on a line of alpha-numeric display 572 as seen in FIG. 14. If agreement between each pair of sensors 86 is found not to be within tolerable limits, ALERT indicator 582 is lit and a message indicating the cause of the ALERT is displayed in place of the mean temperature on alpha-numeric display 572. Also, when the heating elements heat, a conductance test is made by conductance test circuit 620 of the current which flows across the parallel circuit comprising heating elements 492, 494, 496, and 498 of heating plate 14. If the current measured by the conductance test is not within preset limits ALERT indicator 582 is lit and an appropriate message is displayed on alpha-numeric display 572. ALERT indications provide information to the user that a problem exists in instrument 540, but may be treated without discontinuing fluid warming and delivery.

In any circumstances, if sensors 86 measure a temperature which exceeds preset safe level, such as in the range of 39 plus degrees centigrade, or a temperature which is greater than preset limits above the set point temperature, an ALARM condition is initiated. Therefor, ALARM indicator 584 is lit. Also an audio alarm is sounded, unless turned off by alarm toggle switch 538. Other ALARM conditions comprise a detected sensor 86 failure, a means temperature difference between heating plates 12 and 14 which exceeds a preset level for a given set point, and either heating plate 12 or 14 not reaching temperature within a preset period.

In all cases, the reason for an ALARM and for an ALERT is displayed on alpha-numeric display 572. Alpha-numeric display 572 is a time-shared, multiple message display center. During normal operation, display 572 provides a READY indication by displaying top heating plate 12 and bottom heating plate 14 mean measured temperatures.

Electrical control system 680 comprises three interlocks, which, when not properly closed, also generate ALARM conditions. A first interlock 602 detects the presence of top heating plate 12 connected to connector 576. A second interlock 604 detects the presence of bottom heating plate 14 connected to connector 578. A third interlock 606 is provided with a position sensitive switch, not shown, which detects that cassette 20 is in place in instrument 540.

Before using instrument 540, therefore, cassette 20 must be in place, interposed between top heating plate 12 and bottom heating plate 14 in instrument 540. Before inserting cassette 20, frame 590 is raised. As seen in FIG. 14, a heater DISENGAGE switch 556, when depressed, is detected by micro-controller 670. Upon sensing depression of switch 556, micro-controller 670 sends a signal to a driving circuit 630 which relieves pressure communicating through an electrically controlled pneumatic valve 640. A compressed air source 642 provides pressurized fluid to drive air cylinder 588 when valve 640 is open. Cylinder 588 comprises a spring or otherwise powered return which retracts cylinder 588 and thereby raises frame 590 when valve 640 is closed.

When frame 590 is DISENGAGED or raised, limited space is provided to insert cassette 20 laterally between heating plates 12 and 14 as indicated by the direction of arrow 484 in FIG. 13. The separation required for insertion of cassette 20 into instrument 540 is only a distance defined by the length from top surface 404 of foil 400 to the bottom of side support 102, which is much less than the width of a finger of a user for a measure of safety. Once cassette 20 is in place with surface 82 of heating plating plate 14 nesting within medial access opening 108, ENGAGE switch 586, seen in FIG. 16, is depressed, signalling micro-controller 670 to send a signal to driving circuit 630 which closes valve 640 to send compressed air to cylinder 588 and engage frame 590.

Figure 11:
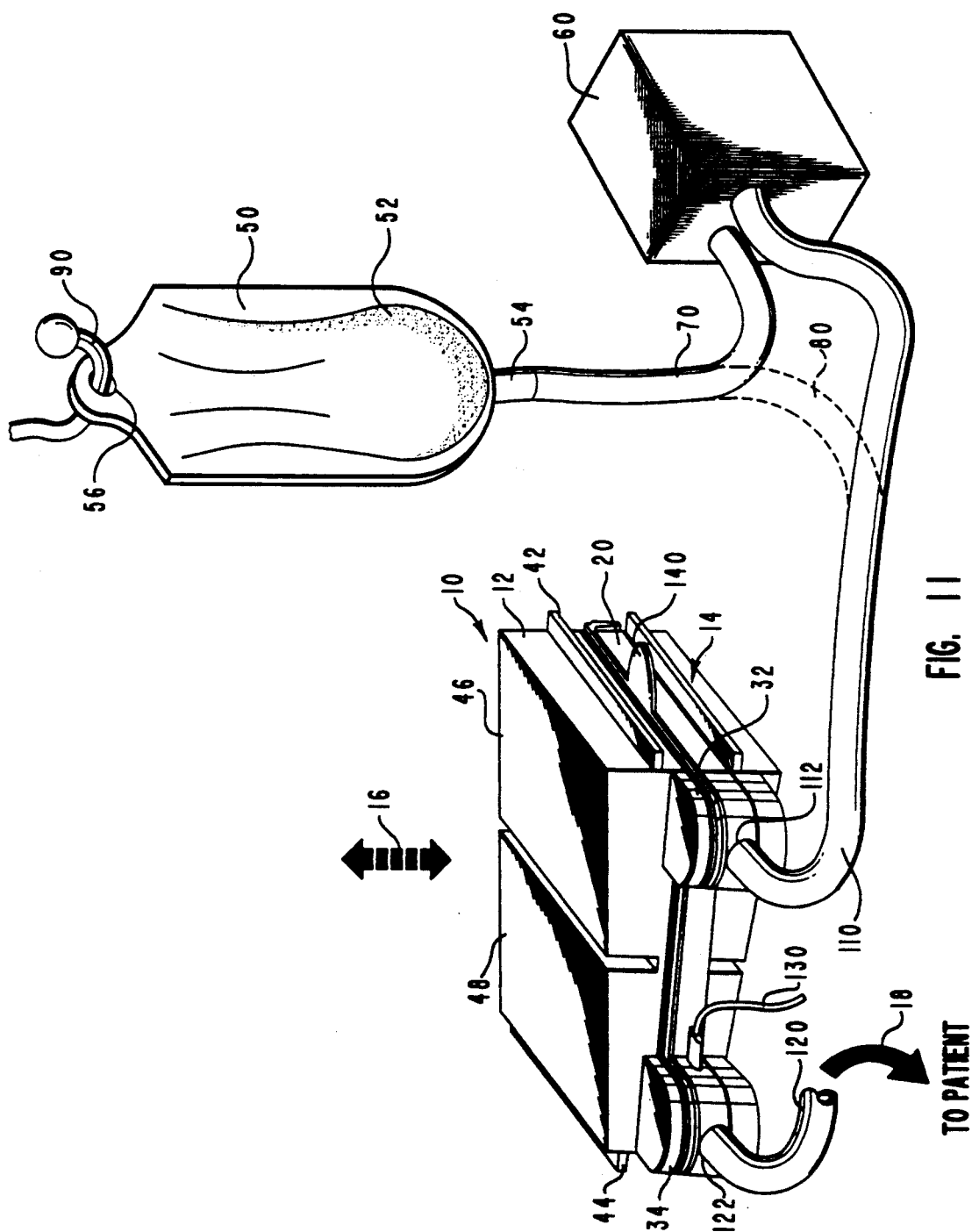
FIG. 11 is a schematic showing major operational components of a fluid heating system.

With cassette 20 disposed in instrument 540, connection is made with a parenteral fluid source and a parenteral fluid pressurizing source as seen schematically in FIG. 11. Physiological fluids 52 are often stored and available in plastic bags 50 comprising a reinforced hole 56 whereby the bag is hung on a hook 90 and an outlet port 54 whereby a connection is made through a tube 70 to a pressure source. Pressure is acquired from a pressure source 60 which is available in many forms in the art. It is common practice to pressurize influent fluids at 300 mm of Hg.

As seen in FIG. 11, a fluid circuit generally comprises a fluid 52 source 50 connected by tubing 70 to a pressure source 60 and therefrom through inlet tubing 110 to cassette 20 which is disposed between heating plates 12 and 14. Fluid flows therethrough to be heated, with effluent flow through outlet tubing 120 to a patient as indicated by arrow 18. It is common practice to interpose a bubble trap between outlet tube 120 and the patient. When a pressure source is not available, a bag 50 can be hung by a from a hook 90 disposed sufficiently above cassette 20 to provide a gravity based static pressure head and allow flow directly from outlet tube 70 through a direct connection indicated by phantom tube 80 to inlet tube 110.

Figure 10:
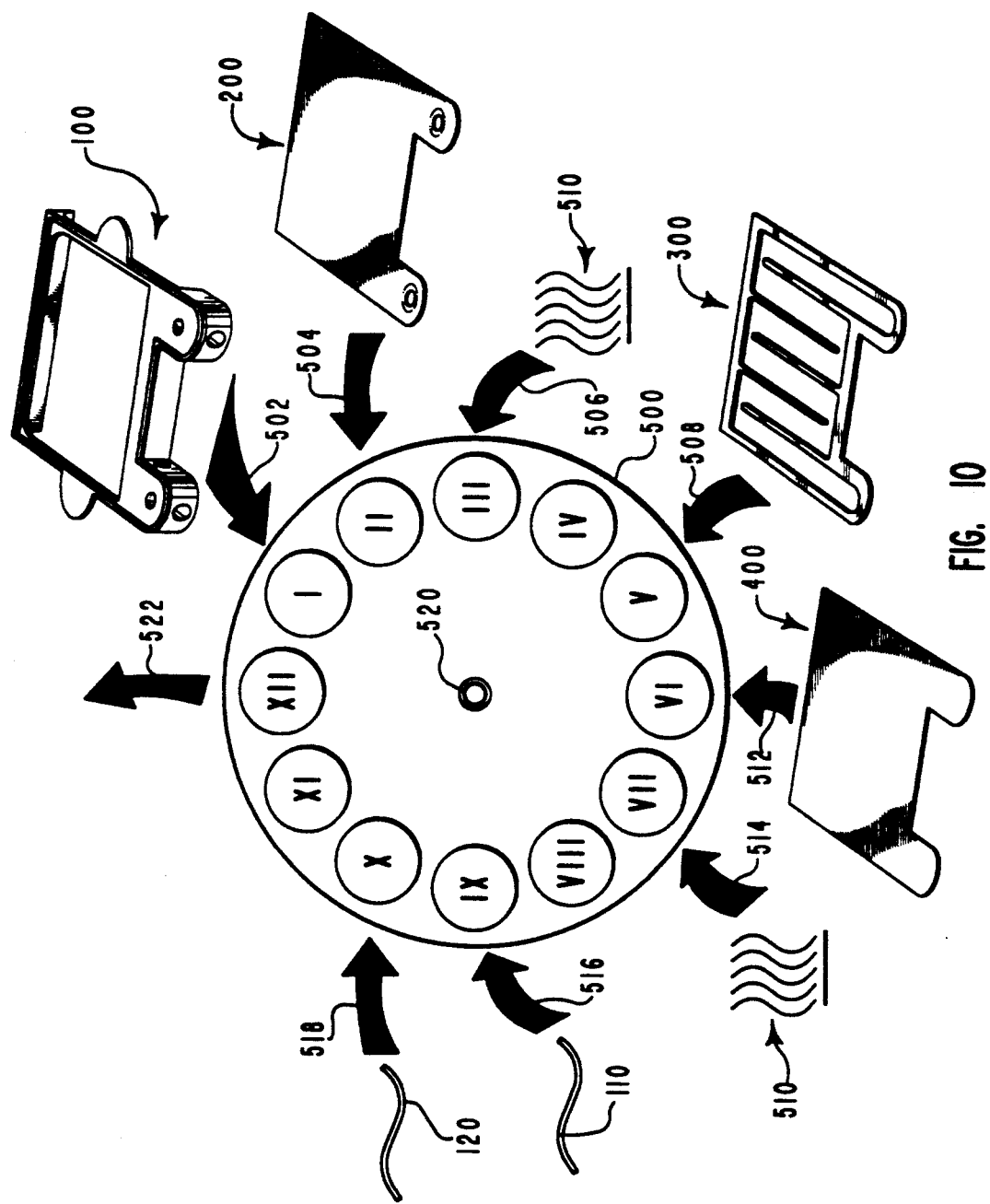
FIG. 10 is a schematic layout wherein steps in a production cycle of the cassette are seen.

A method for making cassette 20 is provided in FIG. 10. An assembly table 500 which rotates about center 520 provides twelve stations which are numbered sequentially with Roman numerals from I XII. At station I, a frame 100 is loaded as indicated by arrow 502. At station II, a bottom foil layer 200 is placed inside rim 106 as previously described and as indicated by arrow 504. Arrow 506 illustrates application of a hater 510 to adhesively bond foil layer 200 to frame 100 at station III. Station IV is a cooling station. At station V, spacer 300 is placed to reside within rim 106 as indicated by arrow 508. At station VI, top foil layer 400 is placed upon spacer 300 as indicated by arrow 512. Application of another heater 510 as indicated by arrow 514 adhesively bonds foil layer 200 and spacer 300 and spacer 300 and foil layer 400 occurs at station VII. Station VIII is a cooling station. A first tube, inlet tube 110, is adhesively attached at Station IX as indicated by arrow 516. At station X, a second tube, outlet tube 120, is similarly adhesively attached as indicated by arrow 528. Station XI is unused, but available for inspection. At station XII, each completed cassette is removed as indicated by arrow 522.

Another currently preferred embodiment of a frame 100' which is similar in shape and function to frame 100 is seen in FIG. 17. Frame 100' provides structural support for the other parts of a cassette 20' in much the same manner as frame 100 provides support for cassette 20, except as explained hereafter. Frame 100' comprises two side supports 168' and 168", distal side member 150", and a proximal side member 770. Disposed proximally from poximal side support 770 is a right pedestal 170', a left pedestal 160', and a ledge 150', each of which is connected to proximal support 770 by a top support plate 104'. Note that pedestals 160' and 170' are the same as pedestals 160 and 170 for frame 100, but disposed as a mirror image in frame 100'. Ledge 150' is disposed between pedestals 160' and 170' as an extension of surface 104', thereby providing a central handle for purposes similar to those of handles 140 and 150 of frame 100. Frame 100' is fabricated by molding or machining from rigid, synthetic resinous material which is substantially inert to parenteral fluids. A material such as cyrolyte may be used for frame 100'.

Each side support 168' and 168" comprises a vertically oriented planar strip essentially disposed across the proximal-to-distal width of cassette 20'. The two supports 168' and 168", in combination, provide a stand for frame 100' and also provide guide members for inserting cassette 20' into a position of use as in described in detail later.

Frame 100' comprises an attachment port 112 for inlet tube 110 in pedestal 160'. Attachment port 112 is sized and shaped to accept plastic inlet tube 110. Similarly, pedestal 170' comprises an attachment port 122 for outlet tube 120. Pedestal 170' comprises another port 132' wherethrough a temperature sensor 130 is inserted and firmly affixed with a leak-proof seal.

Pedestal 160' comprises a right angle flow path 116 as signified by arrows 146 and 164 in FIG. 17. Pedestal 160' comprises an orifice 114 through a lower top surface 144' where inlet flow enters cassette 20'. Frame 100' comprises a thin ridge 142' which is disposed on top support plate 104' around the perimeter of the top of frame 100'. Disposed medially from ridge 142' in top support plate 104' is lower surface 144', separated from ridge 142' by a rim 106'. Lower surface 144' comprises a medial access 108', which is the same as medial access 108 of frame 100 and wherethrough an opening is provided in top plate 104'. The use and function of opening 108' is the same as medial access opening 108 of frame 100, described above.

Pedestal 170' comprises an outlet orifice 124 and right angle flow path 126. However, as seen in FIG. 9, flow path 126 is partially interrupted by a flow restrictor 180 thereby providing a flow path of reduced diameter relative to the diametral size of outlet orifice 124 and inlet orifice 114. Similar to its use in frame 100, restrictor 180 produces a measurable pressure drop across flow path 126 thereby providing a greater than ambient pressure in cassette 20 when pressurized fluid is flowing therethrough.

Pedestal 170' also comprises a temperature sensor port 132' wherein sensor 130, is inserted to measure fluid flow temperature in outlet path 126.

Referring again to FIG. 17, a depression is formed around the edges of orifice 114 in top surface 144' of top plate 104' of such a thickness that an adhesive 162 placed therein fills the depression without rising substantially above surface 144'. A similar depression wherein adhesive 162 is disposed is formed about orifice 124. Adhesive 162 is also disposed on top surface 144' along medial access opening 108'. Adhesive 162 may be a thermal or contact adhesive selected from adhesives which are known and available in the art.

As described for cassette 20, a foil 200, a spacer 300, and a foil 400 is disposed and adhesively attached above frame 100' to form cassette 20' as seen in figure 20. Cassette 20' thereby comprises ledge 150' which provides a handle. In combination, with sides 168' and 168" ledge 150' provides a front entry cassette. Direction of insertion, therefor, is in the direction of arrow 776 (see figure 20) into the front side of instrument 540 which comprises front panel 570.

As seen in FIG. 18, a cross section of a portion of cassette 20' is disposed above low thermal mass heater 14'. Cassette 20' comprises frame 100', lower foil 200, spacer 300, and upper cover foil 400. In use, another low thermal mass heater, similar in structure to low thermal mass heater 14', but disposed for use in the manner of heating plate 12 of cassette 20, is disposed above cassette 20 or 20'. As use of the other low thermal mass heater is substantially the same as the use of heating plate 12 and the structure of the other low thermal mass heater is essentially the same as low thermal mass heater 14', structure and function of the other low thermal mass heater is not further described.

Low thermal mass heater 14' comprises a stand 740, a captured layer of thermal insulation 710, a flexible film heater layer 730 and a heat distribution layer 720. Stand 740 comprises an outer leg 704 on each lateral side of heater 14' and a plurality of inner supports 702. Stand 740 is made from rigid synthetic resinous material.

The film heater layer 730 is disposed above thermal insulation layer 710 which is captured in a recess 712 in the top of stand 740. Thermal insulation layer 710 comprises a relatively thick layer when compared to the thickness of film heater layer 730 and is made from highly thermally insulating material. The insulating material may be paper.

Film heater layer 730, best seen in FIG. 19, comprises a plurality of thin conductors 732 and 734 prepared in a manner similar to that of printed wiring. So made, the resistance of end conductor 732 and 734 is varied end to end to provide an area of greatest heat output where heat absorption by the parenteral fluid flowing through cassette 20 or 20' is the greatest. Film heater layer 730 may be Flexible Thermofoil Heating Element or a Glass Reinforced Silicon Rubber Heater manufactured and distributed by Minco Products, Inc., 7300 Commerce Lane, Minneapolis, Minn. 55432.

Heat distribution layer 720 is disposed at the interface between cassette 20 or 20' and film heater layer 730 and is bonded or otherwise adhesively attached to film heater layer 730. Heat distribution layer 720 comprises sufficient heat capacity to provide a homogeneous temperature at the interface, yet is sufficiently thin the provide a rapid thermal response, to lower foil 200 which comprises a similar pressured surface 206 to surface 722 contact with heat distribution layer 720 as earlier described above for the contact between cassette 20 and heating plate 14. Heat distribution layer 720 comprises a planar pattern similar to the pattern of top surface 82 of heating plate 14 such that the top surface 722 of thermal distribution layer 720 fits within the perimeter of medial access 108 or 108' of cassette 20 or 20', respectively.

Provided as a part of film heater layer 730 is at least one thermal sensor 786 which measures the temperature of the heat distribution layer 720. In the currently preferred embodiment, at least two thermal sensors are used to provide redundancy of measurement whereby a poorly performing sensor 786 is detected and an alert is thereby provided, as earlier described.

Low thermal mass heater 14' comprises a pair of grooves 706, on each side, one of which is seen in FIG. 18. The grooves provide for facile, tongue-in-groove insertion into an instrument in the same manner as guide rails 64 provide insertion for heating plate 14. Electrical connection of low thermal mass heater 14' is made in the same way as heating plate 14 is connected.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A disposable cassette adapted for placement between a pair of heating elements so as to warm parenteral fluids flowing through the cassette for intravenous delivery to a patient, the cassette comprising:

insulative passageway means for insulating, supporting and spacing first and second heat conductive membrane means one from the other, and defining a thin, planar serpentine flow path having top and bottom sides and an inlet end and an outlet end, such that a thin sheet of parenteral fluid enters the inlt end, travels through the serpentine flow path, and exits the outlet end;

a first flexible, heat conductive membrane means supported on one side of said passageway means and providing heat transfer from one of the heating elements to one of the top and bottom sides of the serpentine flow path, said first heat conductive membrane means comprising an inlet port for communicating the parenteral fluid to the inlet end of the serpentine flow path, and an outlet port for exit of the warmed parenteral fluid from the serpentine flow path;

a second flexible, heat conductive membrane means supported on an opposite side of said passageway means so as to be insulated from the first flexible, heat conductive membrane, and providing heat transfer from the other heating element to the other of the top and bottom sides of the serpentine flow path, such that said serpentine flow path is essentially completely covered on the top and bottom sides thereof from the inlet to the outlet ends by the first and second heat conductive membrane means which are insulated and spaced from one another; and support means providing a peripheral framework that encompasses and sealingly receives and holds generally in the plane of the serpentine flow path essentially all of the peripheral edges of the first and second heat conductive membrane means with the insulative passageway means sandwiched therebetween without obstructing contact of the first and second heat conductive membrane means with the pair of heating elements when the cassette is placed therebetween.

2. A disposable cassette as defined in claim 1 wherein said passageway means comprises a unitary member having opposing end and side pieces joined together to form a medial section that is mostly open, the opening of said medial section being divided to form the serpentine flow path by a plurality of path separators alternately extending into the opening from the opposing end pieces.

3. A disposable cassette as defined in claim 2 wherein the first and second heat conductive membrane means are sealingly joined to the unitary member at the opposing end and side pieces and at the path separators on top and bottom surfaces thereof to form an enclosed fluid tight serpentine flow path between the plurality of path separators.

4. A disposable cassette as defined in claims 1 or 3 wherein the first and second heat conductive membrane means are each comprised of a thin, flexible metallic foil.

5. A disposable cassette as defined in claim 4 wherein the metallic foil is silver.

6. A disposable cassette as defined in claim 4 wherein the metallic foil is aluminum.

7. A disposable cassette as defined in claim 4 wherein the metallic foil is silver plated copper.

8. A disposable cassette as defined in claims 1 or 3 wherein the metallic foil is a thin, flexible heat conductive plastic material.

9. A disposable cassette as defined in claim 2 wherein said support means comprises guide means providing sliding engagement onto one of the heating elements.

10. A disposable cassette as defined in claim 2 further comprising sensor means, in communication with the warmed parenteral fluid exiting the serpentine flow path, for detecting the temperature of the warmed parenteral fluid.

11. A disposable cassette as defined in claim 2 further comprising fluid restrictor means for increasing the pressure of the parenteral fluid as the fluid flows through the serpentine flow path, to a pressure higher than ambient atmospheric pressure.

12. An apparatus for heating parenteral fluids for intravenous delivery to a patient, comprising:

a disposable cassette means for transferring heat to parenteral fluids flowing therethrough, the cassette means comprising:

insulating passageway means defining a thin, planar serpentine flow path having top and bottom sides and an inlet end and an outlet end, such that a thin sheet of parenteral fluid enters the inlet end, travels through the serpentine flow path, and exits the outlet end;

a first flexible, heat conductive membrane means supported on one of the top or bottom sides of the insulating passageway means and providing heat transfer to one of the top and bottom sides of the serpentine flow path;

a second flexible, heat conductive membrane means supported on the other of the top or bottom sides of the insulating passageway means so as to be both spaced and insulated from the first flexible, heat conductive membrane means, and providing heat transfer to the other of the top and bottom sides of the serpentine flow path; and support means providing a peripheral framework that sealingly receives and holds the first and second heat conductive membrane means with the passageway means; and heating means in contact with said first and second heat conductive membrane means for generating a gradation of heat energy such that more heat energy is available for transfer to the parenteral fluid at the inlet end of the serpentine flow path than is available for transfer to the parenteral fluid at the outlet end of the serpentine flow path.

13. An apparatus as defined in claim 12 wherein said passageway means comprises a unitary member having opposing end and side pieces joined together to form a medial section that is mostly open, the opening of said medial section being divided to form the serpentine flow path by a plurality of path separators alternately extending into the opening from the opposing end pieces.

14. An apparatus as defined in claim 13 wherein the first and second heat conductive membrane means are sealingly joined to the unitary member at the opposing end and side pieces and at the path separators on top and bottom surfaces thereof to form an enclosed fluid tight serpentine flow path between the plurality of path separators.

15. An apparatus as defined in claims 12 or 14 wherein the first and second heat conductive membrane means or each comprised of a thin, flexible metallic foil.

16. An apparatus as defined in claim 15 wherein the metallic foil is silver.

17. An apparatus as defined in claim 15 wherein the metallic foil is aluminum.

18. An apparatus as defined in claim 15 wherein the metallic foil is silver plated copper.

19. An apparatus as defined in claims 12 or 14 wherein the metallic foil is a thin, flexible heat conductive plastic material.

20. An apparatus as defined in claim 13 wherein said support means comprises guide means providing sliding engagement onto one of the heating elements.

21. An apparatus as defined in claim 13 further comprising sensor means, in communication with the warmed parenteral fluid exiting the serpentine flow path, for detecting the temperature of the warmed parenteral fluid.

22. An apparatus as defined in claim 13 further comprising fluid restrictor means for increasing the pressure of the parenteral fluid as the fluid flows through the serpentine flow path, to a pressure higher than ambient atmospheric pressure.

23. An apparatus as defined in claim 12 wherein said heating means comprises first and second heating blocks, one heating block contracting the first heat conductive membrane means and the other heating block contacting the second heat conductive membrane means.

24. An apparatus as defined in claim 23 wherein each heating block comprises at least two thermally separated sections.

25. An apparatus as defined in claim 24 wherein each section has a plurality of heating element means providing differing energy outputs so as to provide said gradation of heat energy.

26. An apparatus as defined in claim 24 wherein each section comprises at least one heat sensor means for detecting temperature of said section.

27. An apparatus as defined in claim 26 further comprising means for automatically controlling the temperature of each said section based upon a selected temperature.

28. An apparatus for heating parenteral fluids for intravenous delivery to a patient, comprising:
a disposable cassette means for transferring heat to parenteral fluids flowing therethrough, the cassette means comprising:
a unitary, insulating member having opposing end and side pieces joined together to form a medial section that is mostly open, the opening of said medial section being divided to form a serpentine flow path by a plurality of insulating path separators alternately extending into the opening from the opposing end pieces;
first and second heat conductive membrane means sealingly joined to the unitary member at the opposing end and side pieces and at the path separators on top and bottom surfaces thereof to form an enclosed fluid-tight serpentine flow path between the plurality of path separators but without permitting the first and second heat conductive membrane means to contact one another; and
support means providing a peripheral framework that sealingly receives and holds the first and second heat conductive membrane means with the unitary member;
first and second hating blocks, one heating block contacting the first heat conductive membrane means and the other heating block contacting the second heat conductive membrane means; and
heating means for generating at each heating block a gradation of heat energy such that more heat energy is available for transfer to the parenteral fluid at the inlet end of the serpentine flow path than is available for transfer to the parenteral fluid at the outlet end of the serpentine flow path.

29. An apparatus as defined in claim 28 wherein each heating block comprises at least two thermally separated sections.

30. An apparatus as defined in claim 29 wherein each section has a plurality of heating elements or means providing differing energy outputs so as to provide said gradation of heat energy.

31. An apparatus a defined in claim 30 wherein each section comprises at least one heat sensor means for detecting temperature of said section.

32. An apparatus as defined in claim 31 further comprising means for automatically controlling the temperature of each said section based upon a selected temperature.

33. An apparatus as defined in claim 32 further comprising sensor means, in communication with the warmed parenteral fluid exiting the serpentine flow path, for detecting the temperature of the warmed parenteral fluid.

34. An apparatus as defined in claim 33 further comprising fluid restrictor means for increasing the pressure of the parenteral fluid as the fluid flows through the serpentine flow path, to a pressure higher than ambient atmospheric pressure.

35. An apparatus as defined in claim 34 wherein the first and second heat conductive membrane means are each comprised of a thin, flexible metallic foil.

36. An apparatus as defined in claim 35 wherein the metallic foil is silver.

37. An apparatus as defined in claim 35 wherein the metallic foil is aluminum.

38. An apparatus as defined in claim 35 wherein the metallic foil is silver plated copper.

39. An apparatus as defined in claim 34 wherein the first and second heat conductive membrane means are each comprised of a thin, flexible heat conductive plastic material.

40. An apparatus as defined in claim 35 wherein said support means comprises guide means providing sliding engagement onto one of the heating elements.

* * * * *

UNITED STATES PATENT AND TRADEMARK OFFICE
CERTIFICATE OF CORRECTION

PATENT NO. : 5,245,693
DATED : September 14, 1993
INVENTOR(S) : DIXON FORD et al.

It is certified that error appears in the above-indentified patent and that said Letters Patent is hereby corrected as shown below:

```
Column 1, line 26, "varying" should be --vary in--
Column 3, line 14, "The" should be --the--
Column 3, line 43, "its" should be --it--
Column 4, line 21, "plate" should be --plane--
Column 4, line 30, "releasibly" should be --releasably--
Column 4, line 48, "releasibly" should be --releasably--
Column 4, line 50, "releasibly" should be --releasably--
Column 5, line 5, after "exceeds" delete "and"
Column 6, line 13, "on" should be --or--
Column 7, line 49, "an" should be --a--
Column 8, lines 35-36, after "Adhesive 262 may be" insert
--the same type of adhesive material--
Column 9, line 10, "n" should be --in--
Column 9, line 58, "he" should be --the--
Column 10, line 1, "int eh" should be --in the--
Column 10, line 53, "56" should be --566--
Column 11, line 6, after "scope" insert --of--
Column 11, line 17, "Section 346" should be --Section 36--
Column 11, line 19, after "20" insert --and--
Column 11, line 25, "late 12" should be --plate 12--
Column 11, line 38, "releasibly" should be --releasably--
Column 12, line 16, "releasibly" should be --releasably--
```

UNITED STATES PATENT AND TRADEMARK OFFICE
CERTIFICATE OF CORRECTION

PATENT NO. : 5,245,693
DATED : September 14, 1993
INVENTOR(S) : DIXON FORD et al.

It is certified that error appears in the above-indentified patent and that said Letters Patent is hereby corrected as shown below:

```
Column 13, lines 35-36, "Therefor" should be --Therefore--
Column 13, line 39, "means." should be --mean--
Column 14, line 41, delete "by a"
Column 14, line 49, "I XII" should be --I-XII--
Column 14, line 53, "hater 510" should be --heater 510--
Column 15, line 9, "poximal" should be --proximal--
Column 15, line 27, "as in" should be --as is--
Column 16, line 11, "therefor" should be --therefore--
Column 16, line 56, "the" should be --to--
Column 20, line 26, "hating blocks" should be --heating blocks--
```

Signed and Sealed this

Seventeenth Day of June, 1997

BRUCE LEHMAN

*Attest:*

*Attesting Officer*     Commissioner of Patents and Trademarks